United States Patent
Cully et al.

(10) Patent No.: US 7,556,641 B2
(45) Date of Patent: Jul. 7, 2009

(54) DEPLOYMENT SYSTEM FOR AN EXPANDABLE DEVICE

(75) Inventors: Edward H. Cully, Flagstaff, AZ (US); Keith M. Flury, Flagstaff, AZ (US); Michael J. Vonesh, Flagstaff, AZ (US)

(73) Assignee: Gore Enterprise Holdings, Inc., Newark, DE (US)

( * ) Notice: Subject to any disclaimer, the term of this patent is extended or adjusted under 35 U.S.C. 154(b) by 729 days.

(21) Appl. No.: 10/892,934

(22) Filed: Jul. 16, 2004

(65) Prior Publication Data

US 2005/0033402 A1   Feb. 10, 2005

Related U.S. Application Data

(63) Continuation-in-part of application No. 10/637,986, filed on Aug. 8, 2003, which is a continuation-in-part of application No. 10/346,598, filed on Jan. 17, 2003, now Pat. No. 7,198,636.

(51) Int. Cl.
*A61F 2/06* (2006.01)
(52) U.S. Cl. ...................................... 623/1.11
(58) Field of Classification Search ................. 604/181; 623/1.11, 1.12; 606/108
See application file for complete search history.

(56) References Cited

U.S. PATENT DOCUMENTS

| | | | |
|---|---|---|---|
| 4,526,175 A | 7/1985 | Chin et al. | |
| 4,530,698 A | 7/1985 | Goldstein et al. | |
| 4,582,181 A | 4/1986 | Samson | |
| 4,604,094 A | 8/1986 | Shook | |
| 4,608,984 A | 9/1986 | Fogarty | |
| 4,723,936 A | 2/1988 | Buchbinder et al. | |
| 4,730,616 A | 3/1988 | Frisbie et al. | |
| 4,732,152 A | 3/1988 | Wallsten et al. | |
| 4,846,174 A | 7/1989 | Willard et al. | |

(Continued)

FOREIGN PATENT DOCUMENTS

CA   2 335 130   12/1999

(Continued)

*Primary Examiner*—(Jackie) Tan-Uyen T. Ho
*Assistant Examiner*—Gregory A Anderson
(74) *Attorney, Agent, or Firm*—Eric J. Sheets

(57) ABSTRACT

The present invention is directed to a deployment system for an endoluminal device. The deployment system includes a confining sheath placed around a compacted endoluminal device. A deployment line is provided in the system that is an integral extension of the sheath. As the deployment line is actuated, the sheath retracts from around the compacted endoluminal device. As the sheath retracts from around the endoluminal device, material from the sheath may be converted into deployment line. Once the sheath is retracted from around the compacted endoluminal device, the endoluminal device expands in configuration and repairs vascular or cardiac structures of an implant recipient. Any remaining sheath material is removed from the implantation site along with the deployment line. The deployment system also includes an endo-prosthesis mounting member placed between the endoluminal device and an underlying catheter. The endo-prosthesis mounting member serves to cushion and retain the endoluminal device when constrained by the sheath and may assist in expansion of the endoluminal device when unconstrained by the sheath.

The present invention is also directed to a deployment system having a deployment assembly that simultaneously expands an endo-prosthesis mounting member while removing a sheath from an expandable medical device.

8 Claims, 21 Drawing Sheets

U.S. PATENT DOCUMENTS

| | | | |
|---|---|---|---|
| 4,848,343 A | 7/1989 | Wallsten et al. | |
| 4,875,480 A | 10/1989 | Imbert | |
| 4,892,519 A | 1/1990 | Songer et al. | |
| 4,960,411 A | 10/1990 | Buchbinder | |
| 5,114,414 A | 5/1992 | Buchbinder | |
| 5,125,895 A | 6/1992 | Buchbinder et al. | |
| 5,192,290 A | 3/1993 | Hilal | |
| 5,201,757 A | 4/1993 | Heyn et al. | |
| 5,242,441 A | 9/1993 | Avitall | |
| 5,409,495 A | 4/1995 | Osborn | |
| 5,411,509 A | 5/1995 | Hilal | |
| 5,445,646 A | 8/1995 | Euteneuer et al. | |
| 5,456,694 A * | 10/1995 | Marin et al. | 623/1.11 |
| 5,476,589 A | 12/1995 | Bacino | |
| 5,501,694 A | 3/1996 | Ressemann et al. | |
| 5,527,292 A | 6/1996 | Adams et al. | |
| 5,534,007 A | 7/1996 | St. Germain et al. | 606/108 |
| 5,540,707 A | 7/1996 | Ressemann et al. | |
| 5,571,135 A | 11/1996 | Fraser et al. | |
| 5,593,418 A | 1/1997 | Mollenauer | |
| 5,628,783 A | 5/1997 | Quiachon et al. | |
| 5,639,274 A | 6/1997 | Fischell et al. | |
| 5,647,857 A | 7/1997 | Anderson et al. | 604/264 |
| 5,662,703 A | 9/1997 | Yurek et al. | |
| 5,667,490 A | 9/1997 | Keith et al. | |
| 5,690,644 A | 11/1997 | Yurek et al. | |
| 5,693,083 A | 12/1997 | Baker et al. | |
| 5,702,364 A | 12/1997 | Euteneuer et al. | |
| 5,749,920 A | 5/1998 | Quiachon et al. | |
| 5,752,934 A | 5/1998 | Campbell et al. | |
| 5,769,885 A | 6/1998 | Quiachon et al. | |
| 5,772,669 A * | 6/1998 | Vrba | 623/1.11 |
| 5,782,909 A | 7/1998 | Quiachon et al. | |
| 5,795,325 A | 8/1998 | Valley et al. | |
| 5,814,405 A | 9/1998 | Branca et al. | |
| 5,824,044 A | 10/1998 | Quiachon et al. | |
| 5,836,868 A | 11/1998 | Ressemann et al. | |
| 5,843,051 A | 12/1998 | Adams et al. | |
| 5,897,567 A | 4/1999 | Ressemann et al. | |
| 5,944,726 A | 8/1999 | Blaeser et al. | |
| 5,957,973 A | 9/1999 | Quiachon et al. | |
| 5,968,013 A | 10/1999 | Smith et al. | |
| 5,968,069 A | 10/1999 | Dusbabek et al. | |
| 5,989,280 A | 11/1999 | Euteneuer et al. | |
| 6,007,543 A | 12/1999 | Ellis et al. | |
| 6,039,758 A | 3/2000 | Quiachon et al. | |
| 6,059,759 A | 5/2000 | Mottola et al. | |
| 6,059,813 A * | 5/2000 | Vrba et al. | 606/198 |
| 6,077,273 A | 6/2000 | Euteneuer et al. | |
| 6,159,565 A | 12/2000 | Campbell et al. | |
| 6,210,434 B1 | 4/2001 | Quiachon et al. | |
| 6,224,627 B1 | 5/2001 | Armstrong et al. | |
| 6,235,050 B1 | 5/2001 | Quiachon et al. | |
| 6,251,093 B1 | 6/2001 | Valley et al. | |
| 6,287,330 B1 | 9/2001 | Johansson et al. | |
| 6,322,587 B1 | 11/2001 | Quiachon et al. | |
| 6,325,814 B1 | 12/2001 | Euteneuer et al. | |
| 6,346,118 B1 | 2/2002 | Baker et al. | |
| 6,352,561 B1 | 3/2002 | Leopold et al. | |
| 6,355,061 B1 | 3/2002 | Quiachon et al. | |
| 6,371,962 B1 | 4/2002 | Ellis et al. | |
| 6,375,676 B1 | 4/2002 | Cox | |
| 6,391,032 B2 | 5/2002 | Blaeser et al. | |
| 6,447,521 B1 | 9/2002 | Mouw et al. | |
| 6,447,540 B1 | 9/2002 | Fontaine et al. | 623/1.12 |
| 6,530,947 B1 | 3/2003 | Euteneuer et al. | |
| 6,533,806 B1 | 3/2003 | Sullivan et al. | |
| 6,540,778 B1 | 4/2003 | Quiachon et al. | |
| 6,562,063 B1 | 5/2003 | Euteneuer et al. | |
| 6,592,592 B1 | 7/2003 | Cox | |
| 6,610,069 B2 | 8/2003 | Euteneuer et al. | |
| 6,663,660 B2 | 12/2003 | Dusbabek et al. | |
| 6,663,666 B1 | 12/2003 | Quiachon et al. | |
| 6,682,557 B1 | 1/2004 | Quiachon et al. | |
| 6,695,862 B2 | 2/2004 | Cox et al. | |
| 6,709,454 B1 | 3/2004 | Cox et al. | |
| 6,712,827 B2 | 3/2004 | Ellis et al. | |
| 6,755,854 B2 | 6/2004 | Gillick et al. | |
| 6,767,361 B2 | 7/2004 | Quiachon et al. | |
| 6,802,849 B2 | 10/2004 | Blaeser et al. | |
| 6,860,898 B2 | 3/2005 | Stack et al. | |
| 6,893,458 B2 | 5/2005 | Cox et al. | |
| 6,942,682 B2 | 9/2005 | Vrba et al. | |
| 2001/0051822 A1 | 12/2001 | Stack et al. | |
| 2002/0052642 A1 | 5/2002 | Cox et al. | |
| 2002/0099431 A1 | 7/2002 | Armstrong et al. | |
| 2002/0099435 A1 | 7/2002 | Stinson | |
| 2003/0028236 A1 | 2/2003 | Gillick et al. | |
| 2003/0158597 A1 | 8/2003 | Quiachon et al. | |
| 2003/0212451 A1 | 11/2003 | Cox et al. | |
| 2004/0122503 A1 | 6/2004 | Campbell et al. | |
| 2004/0143272 A1 | 7/2004 | Cully et al. | |
| 2004/0143315 A1 | 7/2004 | Bruun et al. | |
| 2004/0153143 A1 | 8/2004 | Quiachon et al. | |
| 2004/0158315 A1 | 8/2004 | Cox et al. | |
| 2005/0015141 A1 | 1/2005 | Quiachon et al. | |
| 2005/0033402 A1 | 2/2005 | Cully et al. | |

FOREIGN PATENT DOCUMENTS

| | | |
|---|---|---|
| CA | 2 329 213 | 7/2000 |
| WO | 00/02503 | 1/2000 |

* cited by examiner

DEPLOYMENT SYSTEM FOR AN EXPANDABLE DEVICE

CROSS REFERENCE TO RELATED APPLICATIONS

This application is a continuation-in-part of co-pending application Ser. No. 10/637,986, filed Aug. 8, 2003, which is a continuation-in-part of application Ser. No. 10/346,598, filed Jan. 17, 2003 now U.S. Pat. No. 7,198,636.

FIELD OF THE INVENTION

The present invention relates generally to implantable medical device assemblies. In particular, the invention relates to means for deploying an expandable medical device within vascular or cardiac structures of an implant recipient.

BACKGROUND OF THE INVENTION

Various implantable medical devices for repairing or reinforcing cardiac and vascular structures have been developed in recent years. Some of these devices can be implanted inside a particular vascular or cardiac structure through so-called interventional, or endovascular, techniques. Interventional techniques involve surgically accessing the vascular system through a conveniently located artery or vein and introducing distal portions of a medical device assembly into the vascular system through the arterial or venous access point. Once the medical device assembly is introduced into the vascular system, it is threaded through the vasculature to an implantation site while proximal portions of the assembly having manually operated control means remain outside the body of the implant recipient. The medical device component of the assembly is then deposited at the implantation site and the remainder of the distal portion of the medical device assembly removed from the vascular system through the access point.

Exemplary interventional medical device assemblies include a catheter. The catheter can be used to precisely position the medical device at an implantation site as well as participate in deployment of the medical device at the implantation site. Some catheters have guidewires running their length to aid in positioning and deployment of the medical device. As an alternative to the guidewire, a catheter may be coaxial with an inner sleeve running inside the length of the catheter. The inner sleeve is used to hold an implantable medical device in position while the outer catheter is pulled back causing deployment of the device. Handles, knobs, or other manually operated control means are attached to the opposite end of the catheter in this type of assembly.

Some implantable medical devices, such as stents, stent-grafts, or other endoluminal devices often require reconfiguration from an initial compacted form to an expanded cylindrical configuration as the devices are deployed at an implantation site. These devices can expand on their own by virtue of the design and composition of their structural elements or through the use of an inflatable balloon placed inside the devices.

Self-expanding endoluminal medical devices are maintained in a compacted configuration in a variety of ways. Some devices are maintained in a compacted configuration by simply confining the compacted devices inside a catheter, or similar tool. Other devices are placed inside a sheath following compaction. In these assemblies, a control line is often used to assist in releasing the endoluminal device from the sheath.

In U.S. Pat. No. 6,352,561, issued to Leopold et al., a sheath is formed around an expandable endoluminal device and a control line used to maintain the sheath around the endoluminal device. The sheath is formed by folding a length of polymeric material in half and stitching the opposing edges together with the control line. The stitching pattern permits the control line to be removed from the sheath by pulling on a proximal end of the control line. As the control line becomes unstitched from the sheath, the endoluminal device is progressively released from confinement within the sheath. The control line is removed from the assembly as a distinct entity while the sheath remains at the implantation site.

In U.S. Pat. No. 5,647,857, issued to Anderson et al., an endoluminal device is held in a collapsed configuration over a catheter by a sheath. The assembly is provided with a control line having a free end and an end attached to a collar component of the catheter. The sheath is removed from the endoluminal device by pulling on the control line. As the control line is pulled, it cuts through and splits the sheath material from distal end to proximal end. As the sheath splits open, the endoluminal device is freed to radially expand. Unlike Leopold et al., the control line remains mechanically attached to the sheath and catheter assembly following deployment of the endoluminal device.

In U.S. Pat. No. 6,447,540, issued to Fontaine et al., a confining sheath is removed from around an endoluminal device with a control line that cuts through and splits the sheath material when pulled by a practitioner, much like Anderson et al. As with Leopold et al, the control line can be completely removed from the assembly as a distinct entity.

In U.S. Pat. No. 5,534,007, issued to St. Germain et al., a single-walled sheath that can collapse and shorten along its length is placed around a stent. As the distal portion of the sheath is retracted, it uncovers the stent. The uncovered stent is free to expand. A control line can be used to exert a pulling force on the collapsible sheath as a means of removing the sheath from the stent. The control line remains attached to the sheath during and subsequent to deployment of the stent.

In U.S. Pat. No. 6,059,813, issued to Vrba et al, a double-walled confinement sheath for an endoluminal device is described. In an assembly made of these components, the endoluminal device is placed over a catheter shaft in a collapsed configuration. An outer tube is placed in slidable relationship over the catheter. The distal end of the outer tube does not extend to cover the endoluminal device. Rather, the double walled sheath is placed over the collapsed endoluminal device. The inner wall of the sheath is attached to the catheter shaft near the proximal end of the endoluminal device. The outer wall of the double-walled sheath is mechanically attached to the outer tube. Movement of the outer tube relative to the catheter causes the outer wall of the sheath to move past the inner wall of the sheath. Movement of the outer tube in the proximal direction causes the sheath to retract and uncover the underlying endoluminal device. As the sheath retracts, the endoluminal device becomes free to expand. A control line is mechanically attached to the outer tube and serves to move the outer tube and retract the sheath.

None of these medical device assemblies utilize a control line that is integral with a sheath. Nor do these assemblies feature a sheath that is convertible to a control line as the sheath is removed from around an expandable medical device, such as an endoluminal device. Such an integral control line and confining sheath would preferably be made of a continuous thin-walled material or composite thereof. The thin-walled material would be flexible and exert minimal restrictions on the flexibility of an underlying expandable medical device. Thin-walled materials would also reduce the profile of the sheath and expandable medical device combination. An integral control line and confining sheath would simplify manufacture of control line-sheath constructs by eliminating the need to mechanically attach the control line to the sheath. An integral control line and confining sheath would also eliminate concerns regarding the reliability of the mechanical attachment of the control line to the sheath. Additionally, inclusion of materials, composites, constructions, and/or assemblies exhibiting compliance, compressibility, resilience, and/or expandability between the sheath-constrained expandable medical device and the delivery catheter would serve to cushion and retain the expandable medical device on a delivery catheter as well as assist in expansion of the expandable medical device in some embodiments.

In some medical applications, it would be advantageous to provide a deployment system or assembly to pre-pressurize an inflatable balloon, or other expandable mounting member, underlying an expandable medical device and maintain or increase the pressure in the balloon as a constraining sheath is gradually removed from the expandable medical device. This would allow for partial expansion of the expandable medical device at an implantation site and permit adjustments in the position of the device in a blood vessel before complete retraction of the sheath and final deployment of the device. In some embodiments, it would be advantageous to introduce a contrast medium into the balloon to provide a background against which an expandable medical device can be better visualized.

There is a need, therefore, for a deployment system or assembly that pressurizes and inflates an endoprosthesis mounting member-component of a catheter-based delivery system while simultaneously retracting a sheath-component of the delivery system from around an underlying expandable medical device.

SUMMARY OF THE INVENTION

The present invention is directed to a deployment system for an expandable medical device, preferably an endoluminal medical device. In preferred embodiments, the expandable medical device is expandable with an "endoprosthesis mounting member" or other dilation means placed within the device. In yet other embodiments, the expandable medical device is an inflatable balloon. The expandable medical device is maintained in a compacted, or collapsed, configuration by a removable constraint, preferably in the form of a retractable sheath. In preferred embodiments, the sheath is removed from around the expandable medical device by applying tension to a deployment line attached to or incorporated into the constraint. In the most preferred embodiment, the deployment line is an integral, continuous, extension of a constraining sheath and is made of the same material as the sheath. As the deployment line is pulled, the sheath is progressively removed from around the expandable medical device. When the sheath has been removed from around a portion of the expandable medical device, that portion of the expandable medical device is freed and can be expanded by an underlying endoprosthesis mounting member. Removal of the sheath is continued until the entire expandable medical device is freed from any radial constraint and self-expanded or expanded by the endoprosthesis mounting member. The deployment line along with any remaining sheath material and the endoprosthesis mounting member are removed from the implantation site through a catheter used to deliver the sheathed expandable medical device and underlying endoprosthesis mounting member to the site.

In embodiments employing an expandable medical device in the form of a stent, the sheath may be removed from around the stent by inflating an endoprosthesis mounting member, or other dilation means—preferably a balloon. The sheath is removed with the aid of the deployment line portion of the present invention and/or a mechanism capable of storing and releasing kinetic energy. As seen in FIG. 13, the mechanism is referred to herein as an "active elastic element (25)" and is preferably in the form of spring elements incorporated into the deployment line portion and/or the sheath portion of the present invention. Alternatively, active elastic elements can be in the form of rubber bands and elastomeric polymers, including fluoroelastomers.

The removable sheath is made of one or more thin, flexible polymeric materials including composites thereof. The sheath ordinarily assumes the form of a continuous thin-walled tube when constraining an expandable medical device, such as an endoluminal device. Such a thin-walled sheath exerts minimal resistance to longitudinal flexing of the underlying expandable medical device. The thin-walled sheath also reduces the profile of the sheath-expandable medical device combination, when compared to conventional constraints. In preferred embodiments, a double-walled tubular sheath is used. Double walls enable the sheath to be retracted from around an expandable medical device by sliding one wall past the other wall. As the sheath is retracted, or unrolled, in this manner, the sheath portion does not rub or scrape against the underlying expandable medical device. This is particularly advantageous when coatings containing lubricants, medications, and/or pharmaceuticals are placed on surfaces of the expandable medical device that could be disrupted by a sheath that rubs or scrapes against the expandable medical device as the sheath is removed from the device.

The deployment line is formed from the same material as the removable sheath and is an integral extension of the sheath material. In some embodiments, the deployment line portion (16) extends from the sheath portion (12, 12a) through a delivery catheter (19) to a deployment assembly (FIGS. 14-17) located at the proximal end of the catheter (FIGS. 3-7). Among these embodiments, the sheath portion extends proximally beyond the expandable medical device toward the distal end of the deployment system (FIG. 5). In preferred embodiments, the sheath extends over the underlying delivery catheter a desired length to a point at which the sheath portion transforms to the deployment line portion (FIG. 7). In more preferred embodiments, the sheath portion extends substantially the entire length of the delivery catheter before transforming into deployment line. In the most preferred embodiment (FIG. 11), at least a portion of the sheath-deployment line construction (12) is enclosed with a secondary catheter (19a) or catheter lumen, or other containment device such as an expanded porous polytetrafluoroethylene tube. In the present invention, a deployment assembly is provided that simultaneously expands an endoprosthesis mounting member while actuating the deployment line. Once the deployment line is actuated, the removable sheath begins to move, or retract, from around the expandable medical device.

In one embodiment, as removed sheath material travels beyond the receding end of the sheath, the sheath begins to become converted to deployment line. Conversion of the sheath into the deployment line usually begins at a point where the tubular sheath breaks apart, separates, and converges into deployment line material. In preferred embodiments, means are provided for initiating or sustaining the conversion of the sheath to deployment line. These means may take the form of perforations, stress risers, or other mechanical weaknesses introduced into the sheath material. The means can also be cutting edges or sharp surfaces on the delivery catheter.

In preferred embodiments, materials, composites, constructions, and/or assemblies exhibiting compliance, compressibility, resilience, and/or expandability are placed between the endoluminal device and the delivery catheter to provide an "endoprosthesis mounting member." An endoprosthesis mounting member serves to cushion the expandable medical device when constrained by the sheath and may assist in expansion of the device when unconstrained. An endoprosthesis mounting member also serves to anchor and retain the expandable medical device in place around an underlying catheter shaft. Anchoring the expandable medical device with an endoprosthesis mounting member eliminates the need for barrier, or retention, means at either end of the expandable medical device. The absence of barrier means contributes to a reduction in the profile of the deployment system as well as increasing the flexibility of the distal portion of the system. The present invention can also be provided with an additional catheter or catheter lumen for the sheath-deployment line in order to prevent the deployment line portion from leaving the general path established by the delivery catheter. The preferred endoprosthesis mounting member is in the form of an inflatable, or otherwise expandable, balloon. The present invention can also be used alone or in combination with other expandable medical device delivery means. Multiple expandable medical devices can also be delivered with the present invention.

In the present invention, the deployment system uses the endoprosthesis mounting member component of a catheter-based delivery system to exert radial force on an overlying expandable medical device, while simultaneously retracting a sheath-component of the delivery system from around the underlying expandable medical device. By allowing the expandable medical device to be gradually deployed in this manner, adjustments in the position of the device in a patient's vasculature can be made before final deployment of the device. In addition, the deployment system is particularly useful with expandable medical devices that do not expand completely or as rapidly as desired. In some embodiments, the deployment assembly includes a contrast medium placed within the endoprosthesis mounting member to provide a background against which an expandable medical device can be better imaged.

Accordingly, one embodiment of the present invention is an implantation system for a medical device comprising an endoprosthesis mounting member, an expandable medical device placed over said endoprosthesis mounting member, a constraint placed over at least a portion of said expandable medical device, and a delivery catheter incorporating said endoprosthesis mounting member, constraint, and expandable medical device, wherein said expandable medical device is deployed by simultaneous retraction of said constraint from said expandable medical device and expansion of said endoprosthesis mounting member.

In another embodiment, the present invention is a medical device deployment system comprising a catheter tube having a proximal end, a length, and a distal end, an endoprosthesis mounting member placed on said distal end of said catheter tube, and an expandable medical device placed over said endoprosthesis mounting member and covered with an overlying retractable sheath, said sheath incorporating a deployment line running inside said catheter tube and attached to an actuator at said proximal end of said catheter tube, wherein said actuator is coupled to a means in fluid communication with a lumen of said endoprosthesis mounting member for expanding said endoprosthesis mounting member, whereby said endoprosthesis mounting member is expanded simultaneously with retraction of said overlying sheath from said expandable medical device.

In yet another embodiment, the present invention is a deployment assembly for a catheter-based delivery system comprising a container defining a first pressurizable chamber, said first pressurizable chamber having an opening therein configured to attach to a delivery catheter having an endoprosthesis mounting member incorporated thereon and provide fluid communication between said first pressurizable chamber and a lumen of said endoprosthesis mounting member, a movable plunger placed within said first pressurizable chamber to establish and maintain fluid pressure in said endoprosthesis mounting member lumen when said plunger is moved, and a deployment line actuator coupled to said movable plunger.

These and other embodiments can also include a pressure relief valve in fluid communication with a pressurizing chamber to prevent over pressurization of an endoprosthesis mounting member. Enclosed gas bladders, or other "pressure capacitors," can also be placed in a pressurizing chamber to help maintain pressurization of an endoprosthesis mounting member.

These enhanced features and other attributes of the deployment system of the present invention are better understood through review of the following specification.

DETAILED DESCRIPTION OF THE INVENTION

Figure 12:
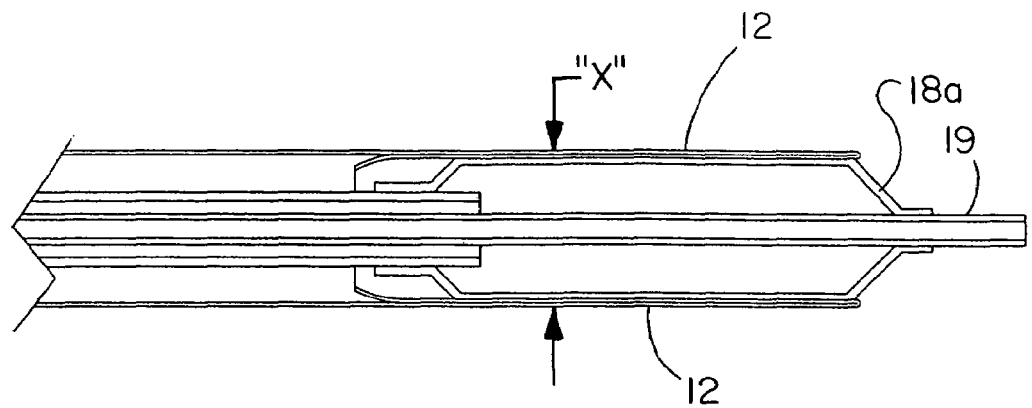
FIG. 12 illustrates a longitudinal cross-section of the present invention showing an expandable medical device in the form of a collapsed and folded inflatable balloon having a first dimension confined to a second dimension with a sheath-deployment line of the invention.
Figure 12:
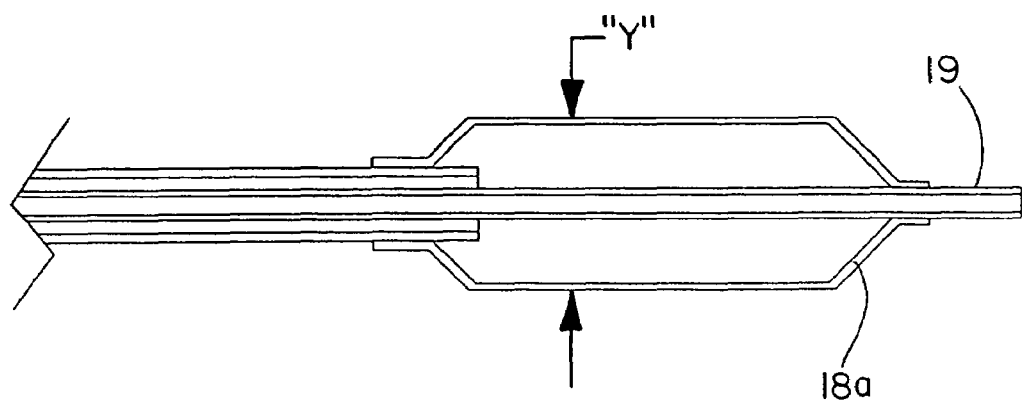
Figure 13:
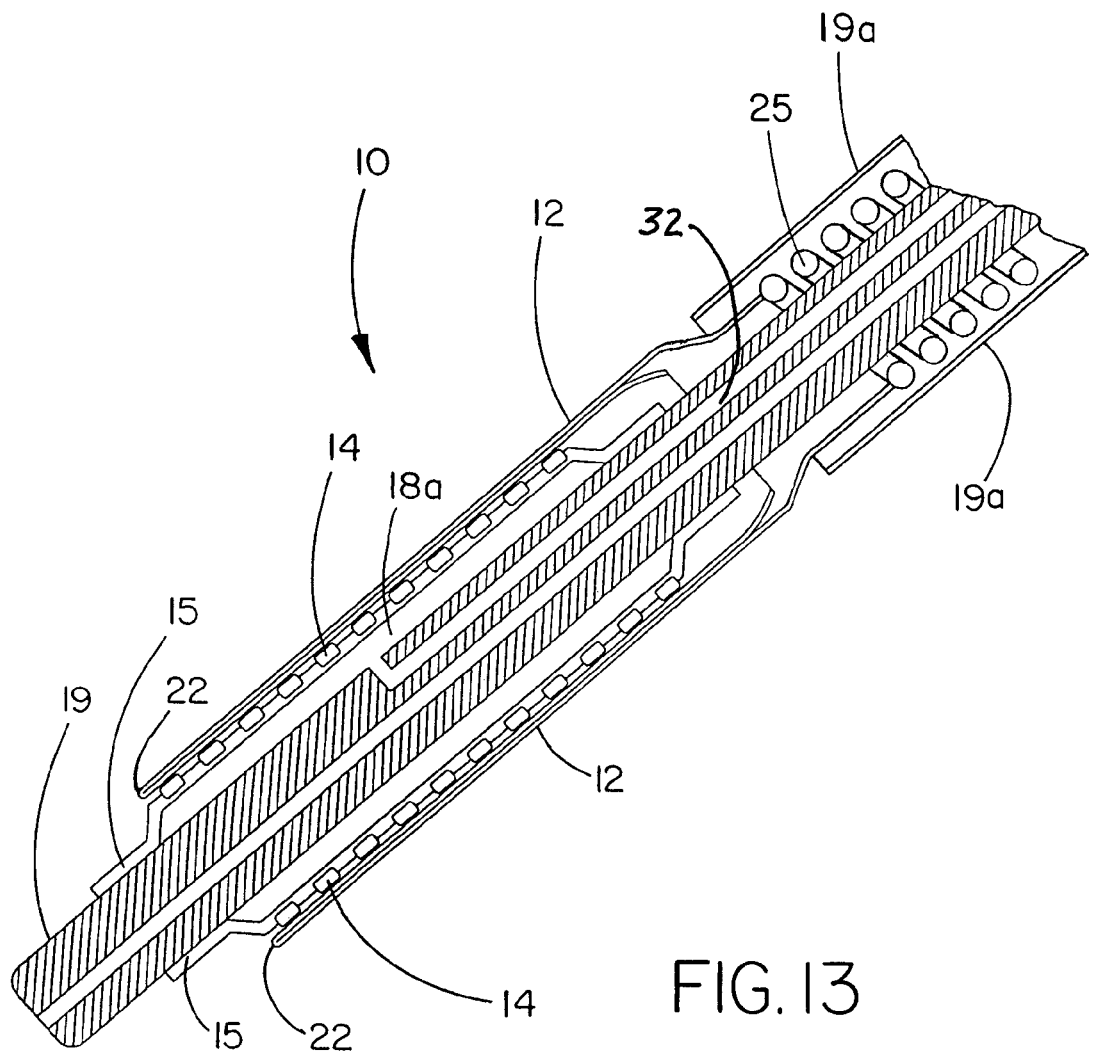
FIG. 13 illustrates a cross-section of the present invention showing an active elastic element attached to the sheath portion of the present invention as a means to remove the sheath from around an expandable medical device.
Figure 14:
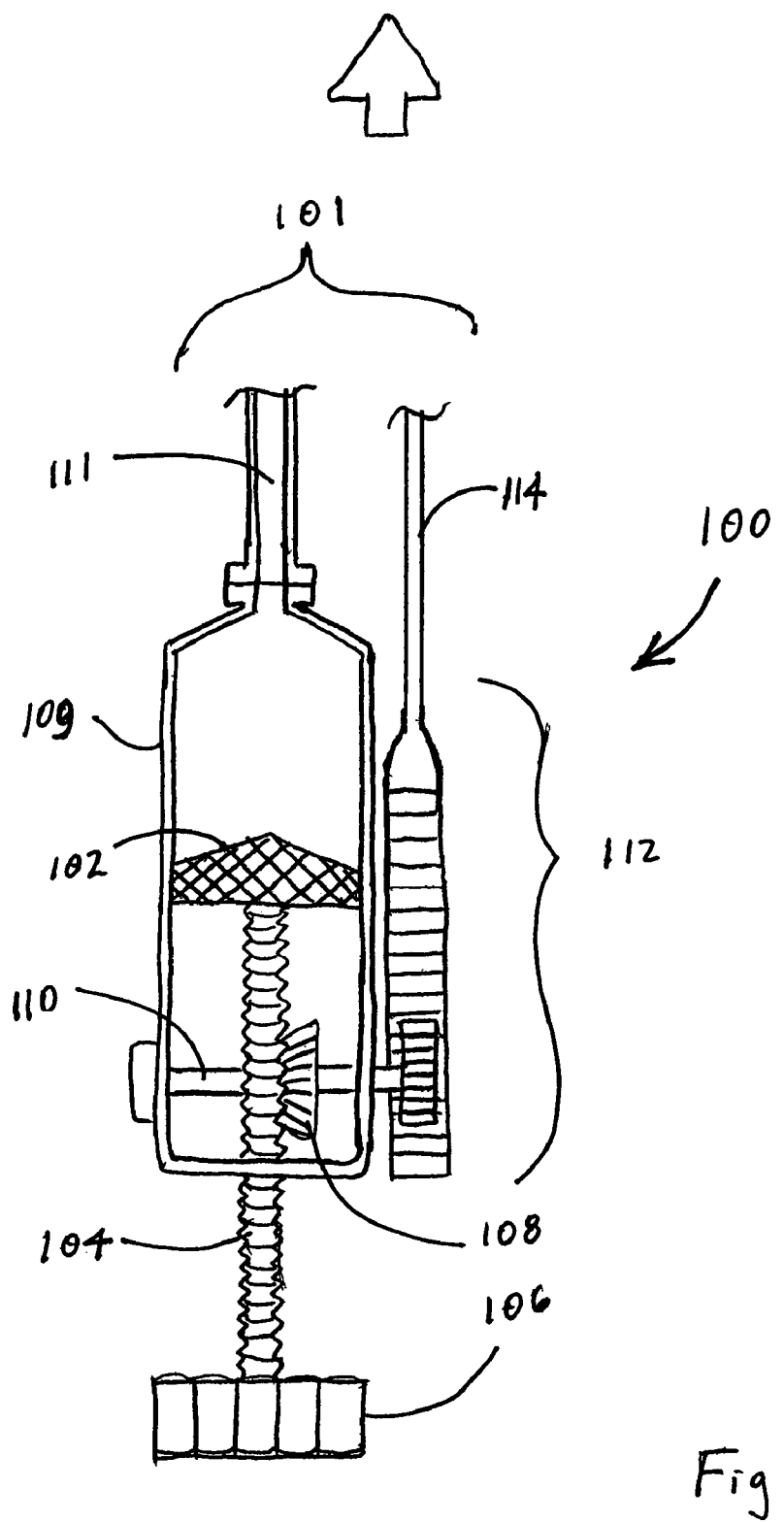
FIG. 14 illustrates a deployment assembly of the present invention having a chamber in fluid communication with a catheter lumen and a plunger in the chamber for pressurizing and inflating an endoprosthesis mounting member. The plunger is coupled to a rack and pinion gear combination through an axle and bevel gear. In practice, actuation of the plunger simultaneously pressurizes and inflates an endoprosthesis mounting member while actuating the pinion gear to move the rack and retract a deployment line or rod attached to, or incorporated into, a sheath component of the deployment system.
Figure 15:
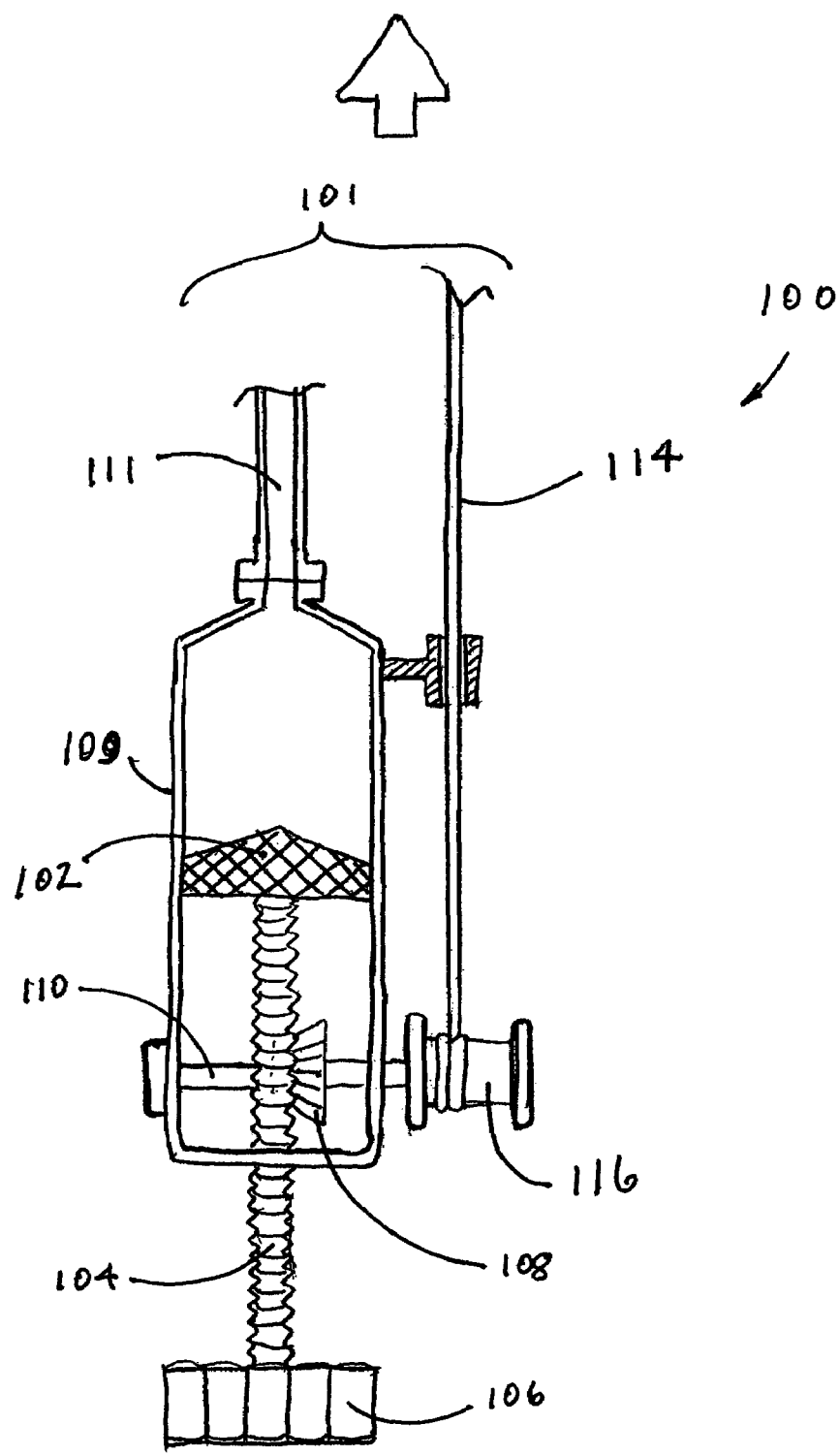
FIG. 15 illustrates a deployment assembly of the present invention showing a chamber in fluid communication with a catheter lumen and a plunger in the chamber for pressurizing and inflating an endoprosthesis mounting member. The plunger is coupled to a spool, reel, or drum, through an axle and bevel gear. In practice, actuation of the plunger simultaneously pressurizes and inflates an endoprosthesis mounting member and rotates the spool to retract a deployment line or rod attached to, or incorporated into, a sheath component of the deployment system.
Figure 16:
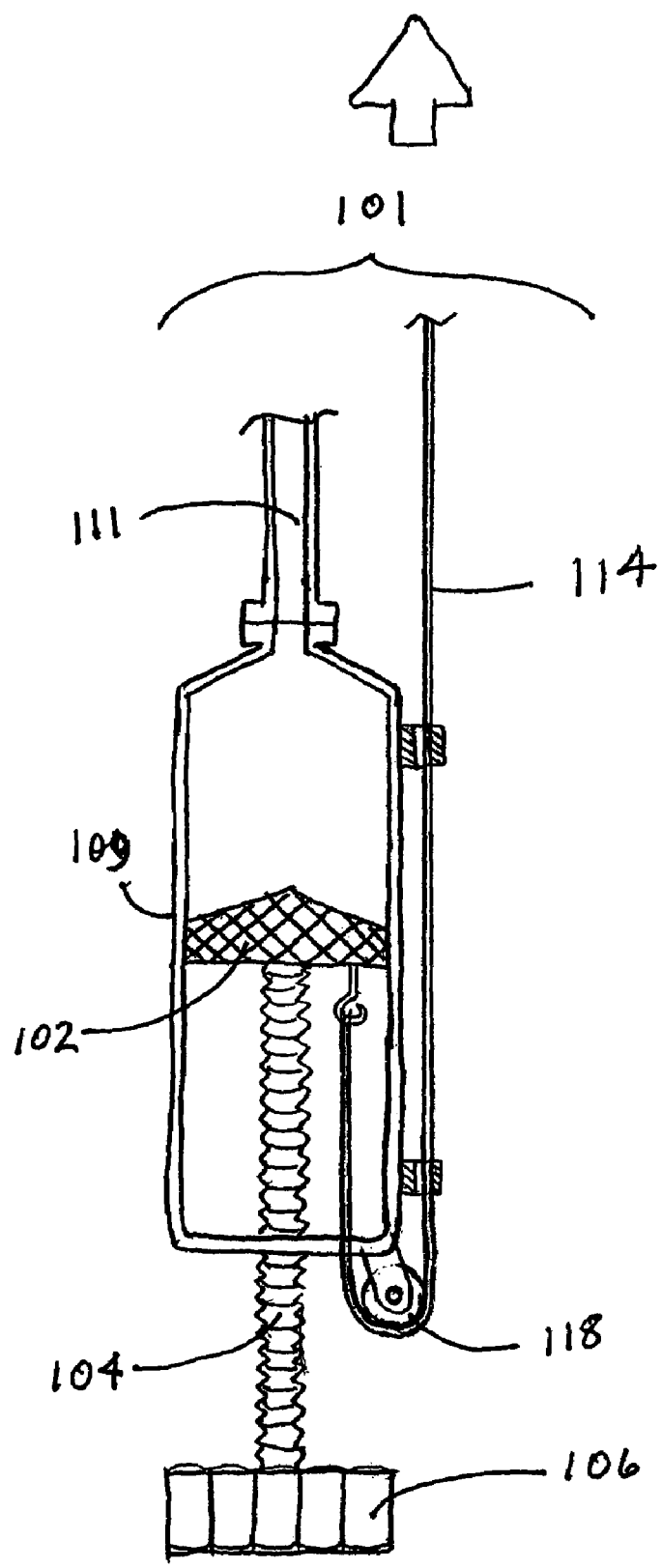
FIG. 16 illustrates a deployment assembly of the present invention showing a chamber in fluid communication with a catheter lumen and a plunger in the chamber for pressurizing and inflating an endoprosthesis mounting member. The plunger is coupled to a deployment line, rod, or retractable sheath through a pulley. In practice, actuation of the plunger simultaneously pressurizes and inflates an inflatable balloon and moves the deployment line, rod, or retractable sheath through the pulley to retract the deployment line, rod, or retractable sheath component of the deployment system.
Figure 17:
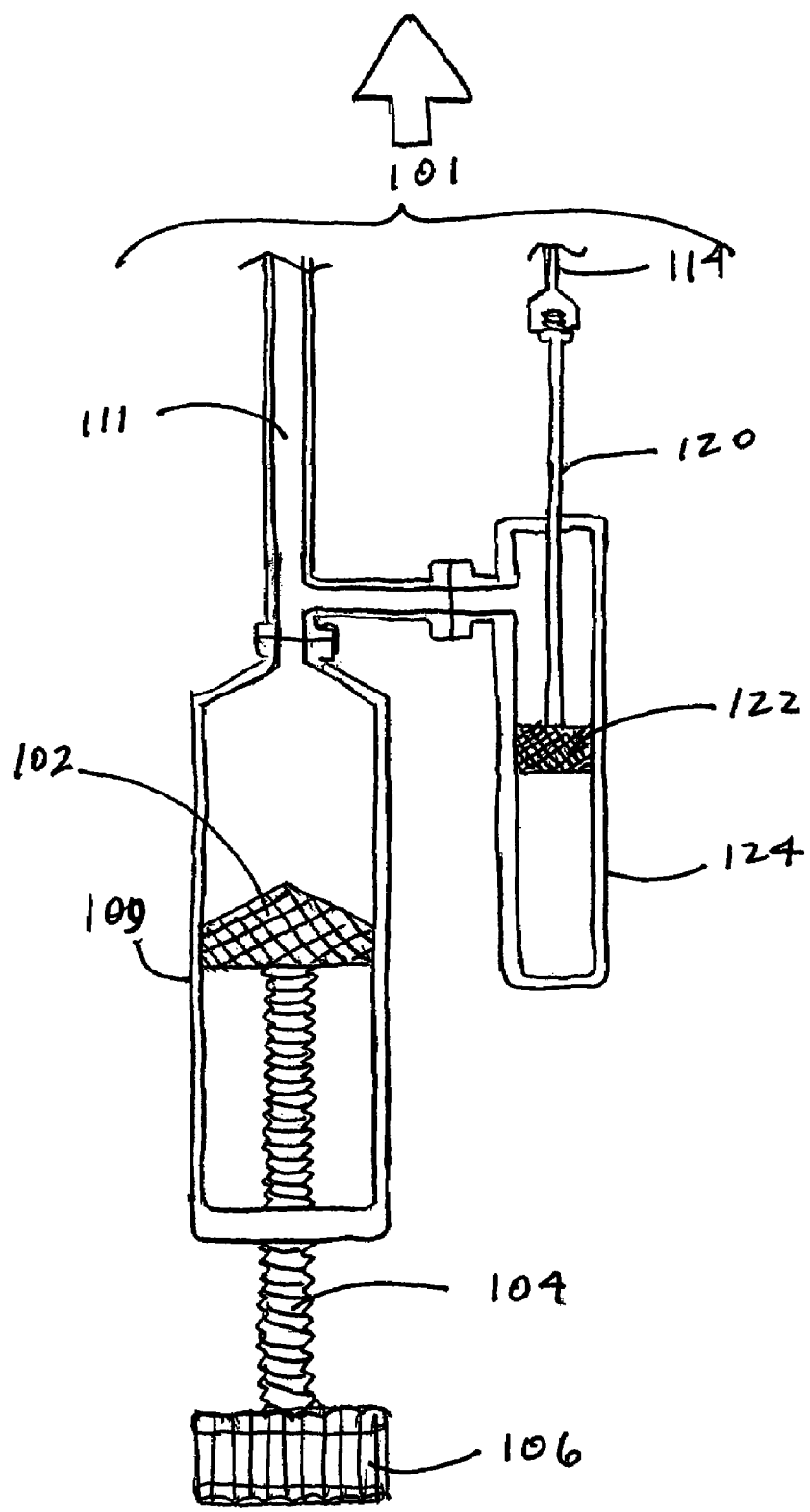
FIG. 17 illustrates a deployment assembly of the present invention showing a first chamber in fluid communication with a catheter lumen and a plunger in the chamber for pressurizing and inflating an inflatable endoprosthesis mounting member. A second chamber is attached to the assembly in fluid communication with the first chamber and catheter lumen. A piston is placed in the second chamber and is attached to a deployment line, rod, or retractable sheath component of the deployment system. In practice, actuation of the plunger simultaneously pressurizes and inflates an inflatable endoprosthesis mounting member while moving the piston to retract the deployment line, rod, or retractable sheath component of the deployment system.

The present invention is directed to a deployment system for an expandable medical device, such as an endoluminal device, having a removable sheath with a deployment line or filament that is an integral part of the sheath. As indicated by the relative difference in the space between the "x" arrows and the "y" arrows in FIG. 12, the sheath portion (12) confines the endoluminal device (18a) to a smaller profile than is possible without the sheath. The sheath radially confines, or constrains, the expandable medical device in a compacted or collapsed configuration during storage and introduction into a patient's vascular system. The constraining sheath maintains the expandable medical device in a compacted configuration until the device is delivered with a catheter to an implantation site in a vascular or cardiac structure. At the time of deployment, the sheath is retracted from the expandable medical device. In some embodiments, sheath material may be converted into deployment line material as the sheath is removed from the expandable medical device. As the sheath is removed from the expandable medical device, the expandable medical device is freed to expand. Once freed from the confining sheath, the expandable medical device may expand spontaneously or with the assistance of an endoprosthesis mounting member. Any remaining sheath material may be removed from the implantation site along with the deployment line.

The deployment system of the present invention permits retraction of the constraining sheath simultaneously with expansion of an endoprosthesis mounting member. The present invention is also directed to a deployment assembly that accomplishes simultaneous expansion of an endoprosthesis mounting member and removal of a constraining sheath from an expandable medical device.

Figure 3:
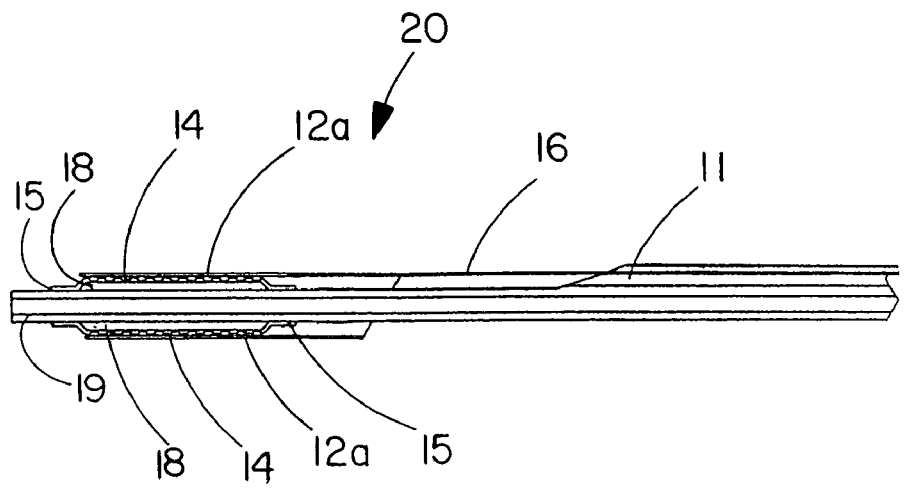
FIG. 3 illustrates a longitudinal cross-section of the present invention.
Figure 3A:
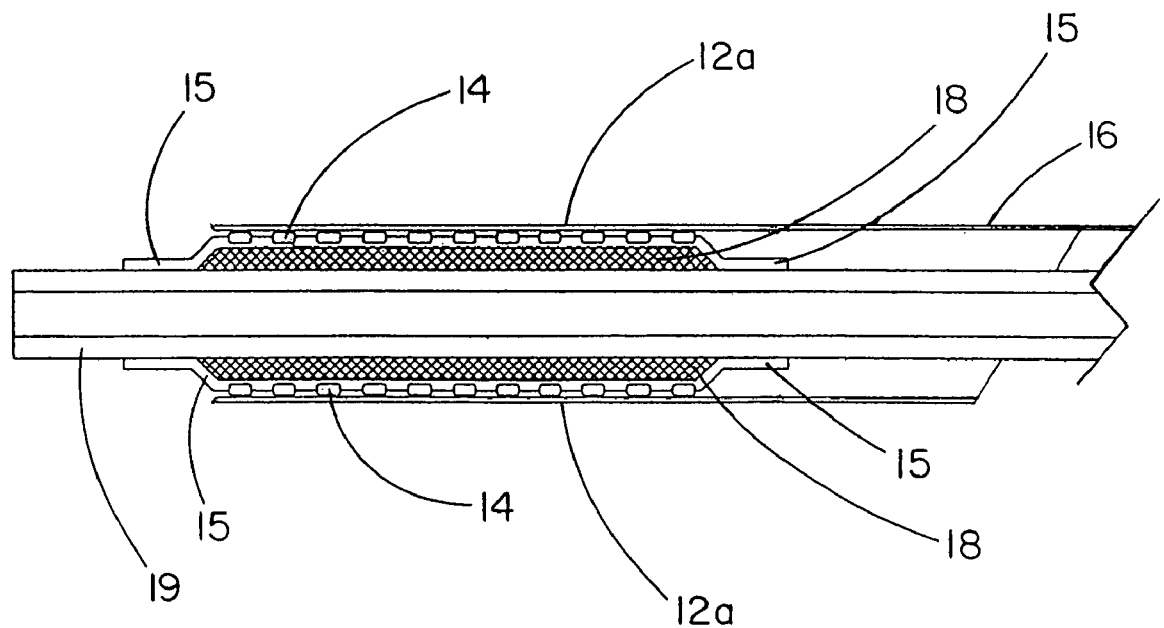
FIG. 3A is an enlarged view of FIG. 3.

The integral sheath-deployment line is preferably a flexible polymeric material that is continuous along the length of the construct. Preferably, the physical and mechanical properties of the sheath portion are such that they are uniform and homogeneous throughout the length of the sheath portion used to constrain the expandable medical device. Since most expandable medical devices are generally circularly cylindrical in form, the sheath is preferably tubular in shape in order to enclose most or all of the expandable medical device. Conical, tapered, or other suitable shapes for the sheath are also contemplated in the present invention. Flexibility of the sheath is enhanced by making the walls of the sheath as thin as practicable. In one embodiment of the present invention (20), the tubular sheath portion (12a) of the sheath-deployment line has a single wall (FIG. 3). The deployment line portion can extend from either end of the single-walled sheath (12a). When the sheath portion is retracted from around an expandable medical device, the length of retracted sheath is substantially equal to the length of deployment line displaced during deployment of the expandable medical device.

Figure 1:
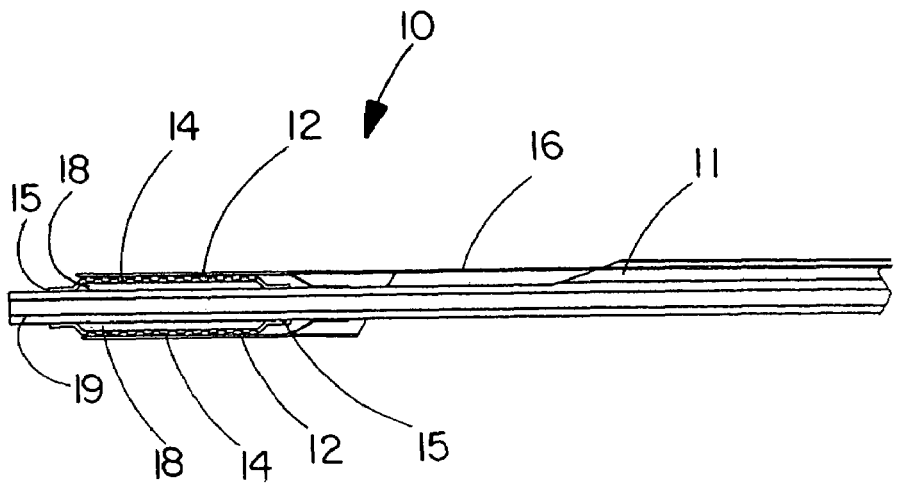
FIG. 1 illustrates a longitudinal cross-section of the present invention.
Figure 1A:
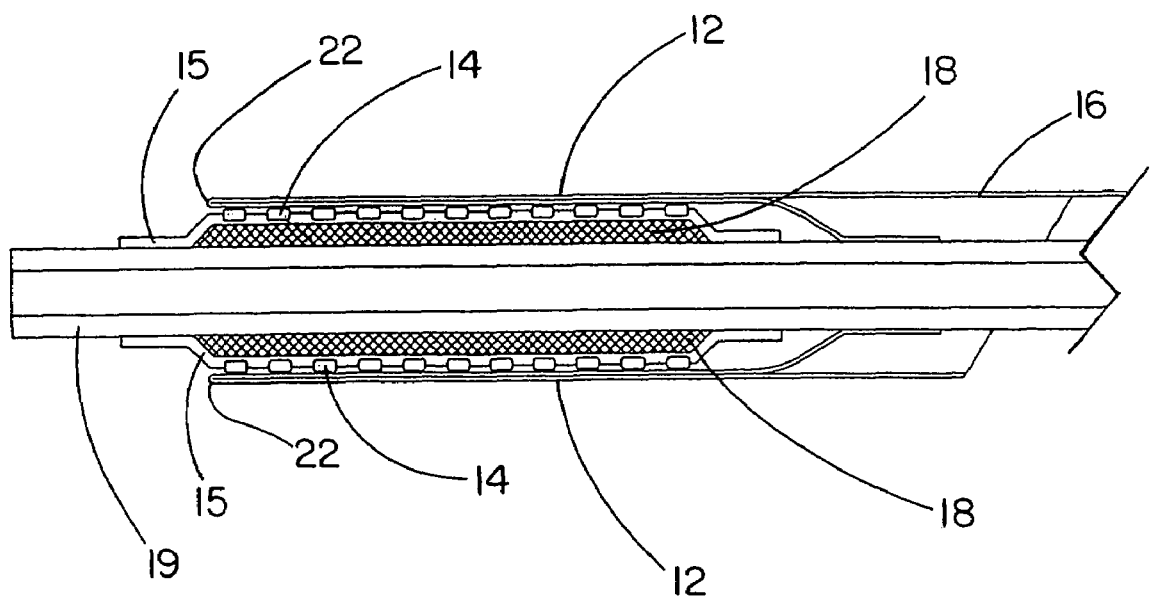
FIG. 1A is an enlarged view of FIG. 1.
Figure 2:
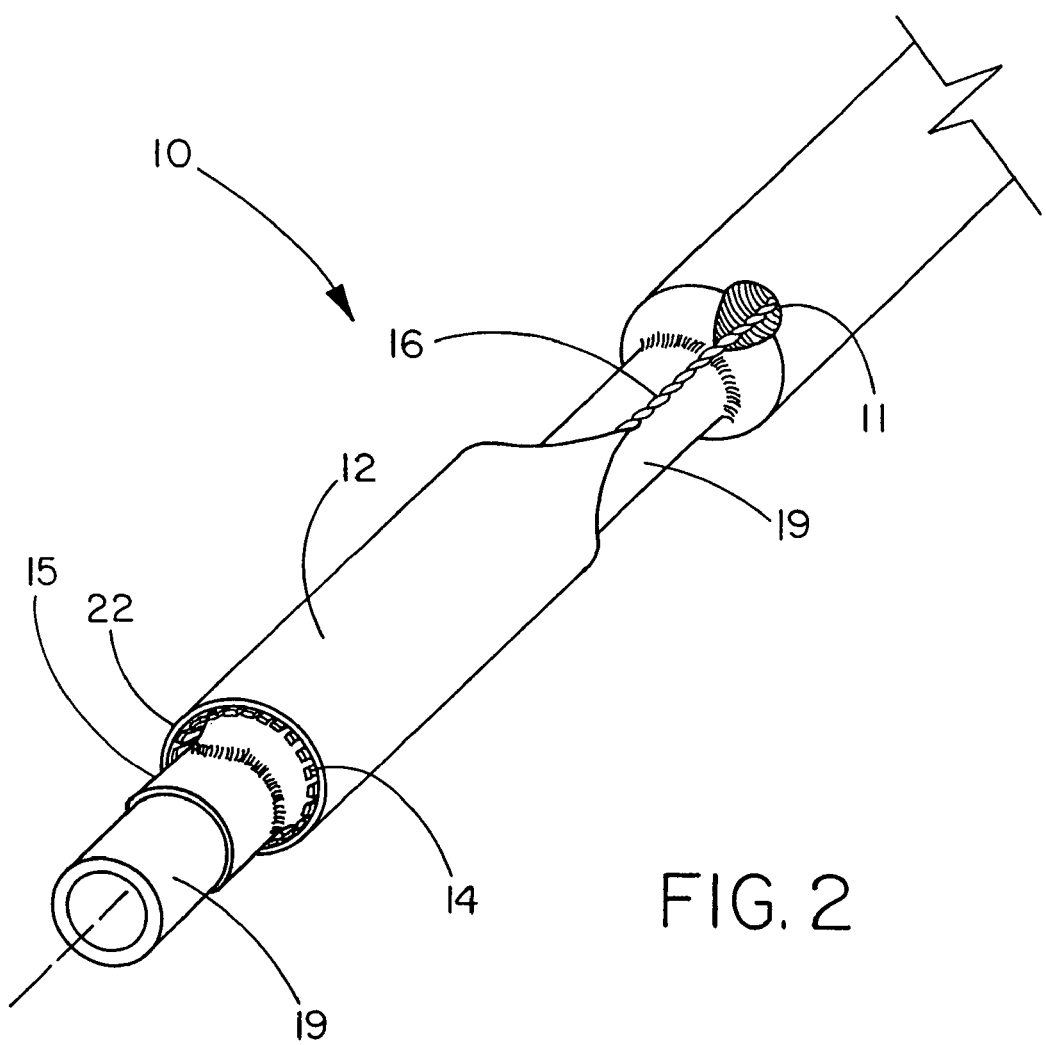
FIG. 2 illustrates a perspective view of the present invention.
Figure 4:
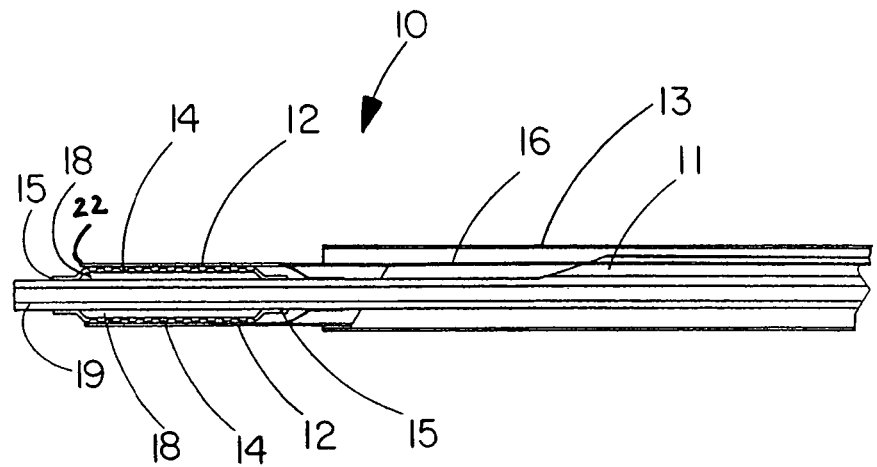
FIG. 4 illustrates a longitudinal cross-section of the present invention.
Figure 4A:
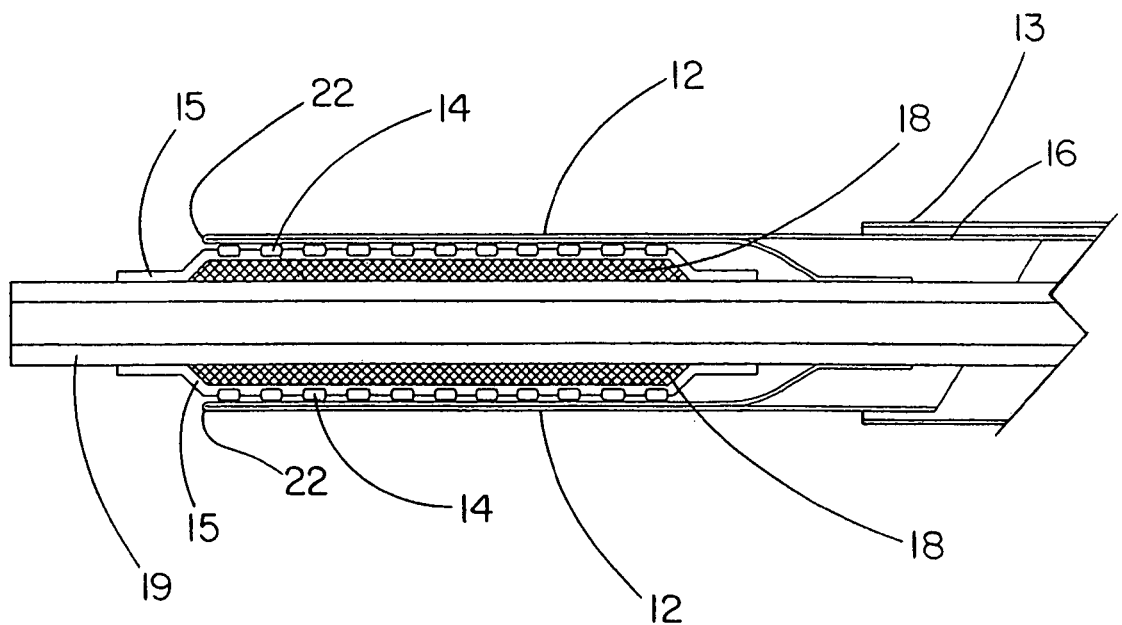
FIG. 4A is an enlarged view of FIG. 4.

In another embodiment of the present invention (10), the sheath portion (12) of the sheath-deployment line has a double wall (FIGS. 1, 2, and 4-11). In a preferred embodiment, the double walled-sheath portion (12) is made of a polymeric material that is folded on itself. The double-walled sheath portion is placed over the expandable medical device (14) so that the fold (22) is positioned at the distal end (i.e., farthest from the deployment assembly) of the sheath portion (12). The inner wall of the sheath portion may be anchored to part of an underlying delivery catheter (19) proximal to the expandable medical device (14). In preferred embodiments, the sheath portion (12) is not attached to the delivery catheter (19). The proximal end of the outer wall of the sheath has at least one portion, or integral extension, that is convertible to deployment line (16). Space between the walls of the double-walled sheath portion can be filled with fluids, lubricants, pharmaceutical compositions, and/or combinations thereof. The deployment line (16) is routed through the delivery catheter (19) to a deployment assembly of the present invention (e.g. FIGS. 14-17) located at the proximal end of the deployment system (10). Alternatively, a separate catheter (13) or catheter lumen (11) is provided for the deployment line (FIGS. 4 and 1, respectively). These embodiments provide additional containment of the deployment line portion, particularly when bends or curves in a patient's vasculature having small radii are anticipated. In the most preferred embodiment (FIG. 11), the sheath portion of the sheath-deployment line construction extends substantially the entire length of the delivery catheter (19) and is confined within a separate catheter (19a) or catheter lumen. The deployment line portion is formed near the proximal end of the deployment system and is attached to a deployment assembly (e.g. FIGS. 14-17).

Preferably, the physical and mechanical properties of the sheath portion are such that they are uniform and homogeneous throughout the length of the sheath portion used to constrain the expandable medical device. When the sheath portion is retracted from around an expandable medical device, the length of retracted sheath is essentially half the length of deployment line displaced during deployment of the expandable medical device. This two to one ratio (2:1) of length of deployment line removed to length of sheath material removed reduces the effect of too rapid or strong a pull on the deployment line on release of the expandable medical device from the sheath.

Fluoropolymer materials are preferred for making the retractable tubular constraining sheath-deployment line constructs of the present invention. Fluoropolymer materials used in the present invention are strong, thin, and lubricious. The lubriciousness of the fluoropolymer materials is especially advantageous in embodiments utilizing a sheath-deployment line having walls that slide past one another or over an expandable medical device. Particularly preferred fluoropolymer materials are porous expanded polytetrafluoroethylene materials alone or in combination with fluorinated ethylene propylene materials. Most preferred fluoropolymer materials are strong and thin, such as those described in Example 2, infra. The sheath-deployment line is made by constructing an appropriate tube from layers of film and/or membrane. The sheath-deployment line may also be constructed from extrusions of polymeric materials. The extrusions can be used alone or in combination with film/membrane materials. Once constructed, a significant portion of the tube is rendered filamentous by rolling and heating.

Figures 5, 5A:
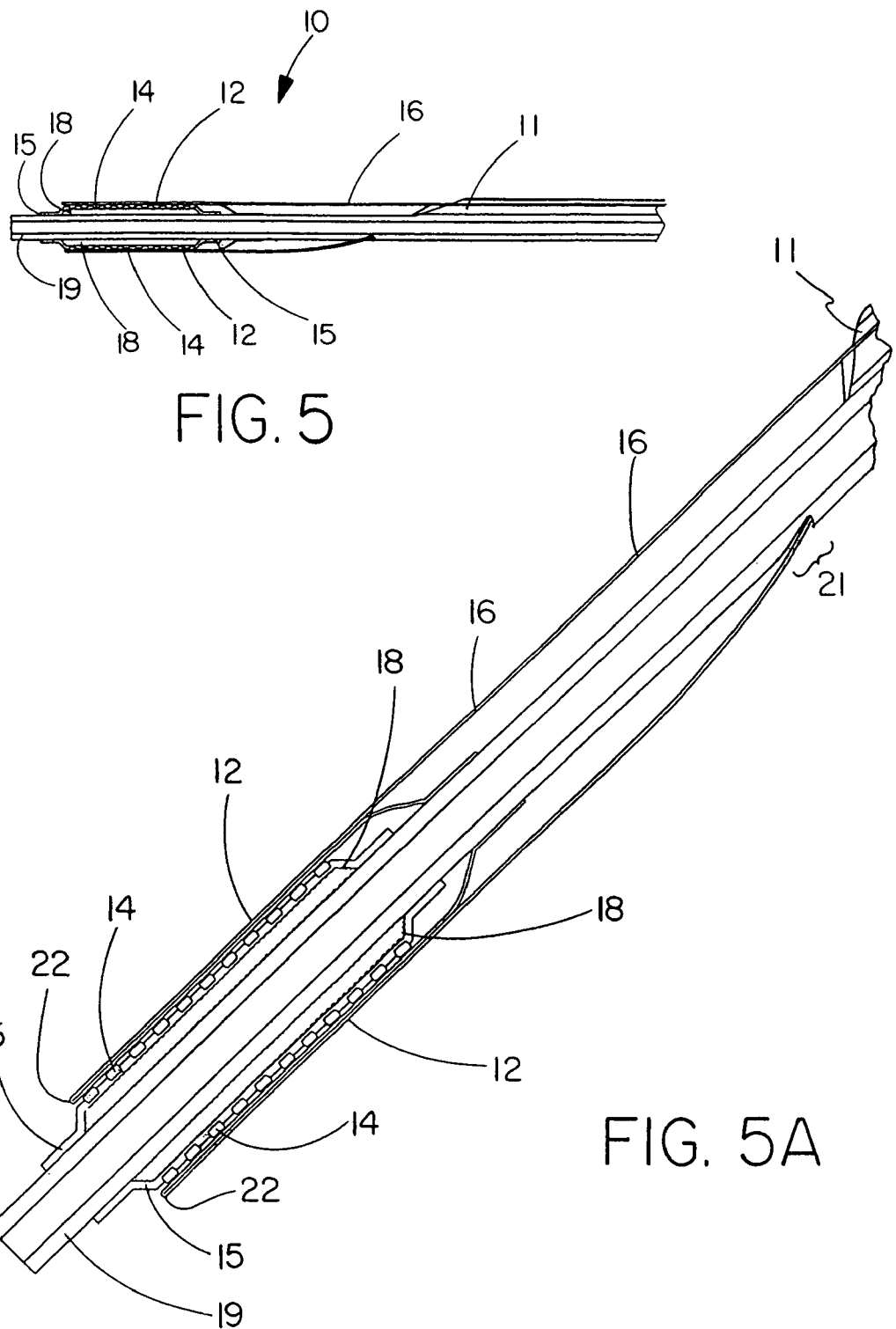
FIG. 5 illustrates a longitudinal cross-section of the present invention.
FIG. 5A is an enlarged view of FIG. 5.
Figure 6:
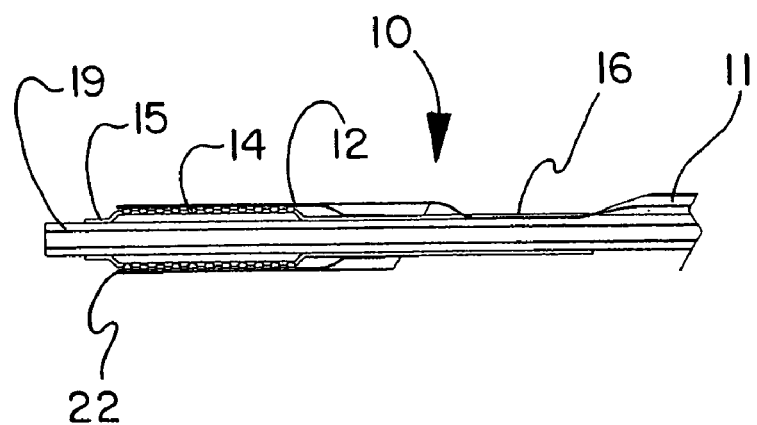
FIG. 6 illustrates a longitudinal cross-section of the present invention.
Figure 6A:
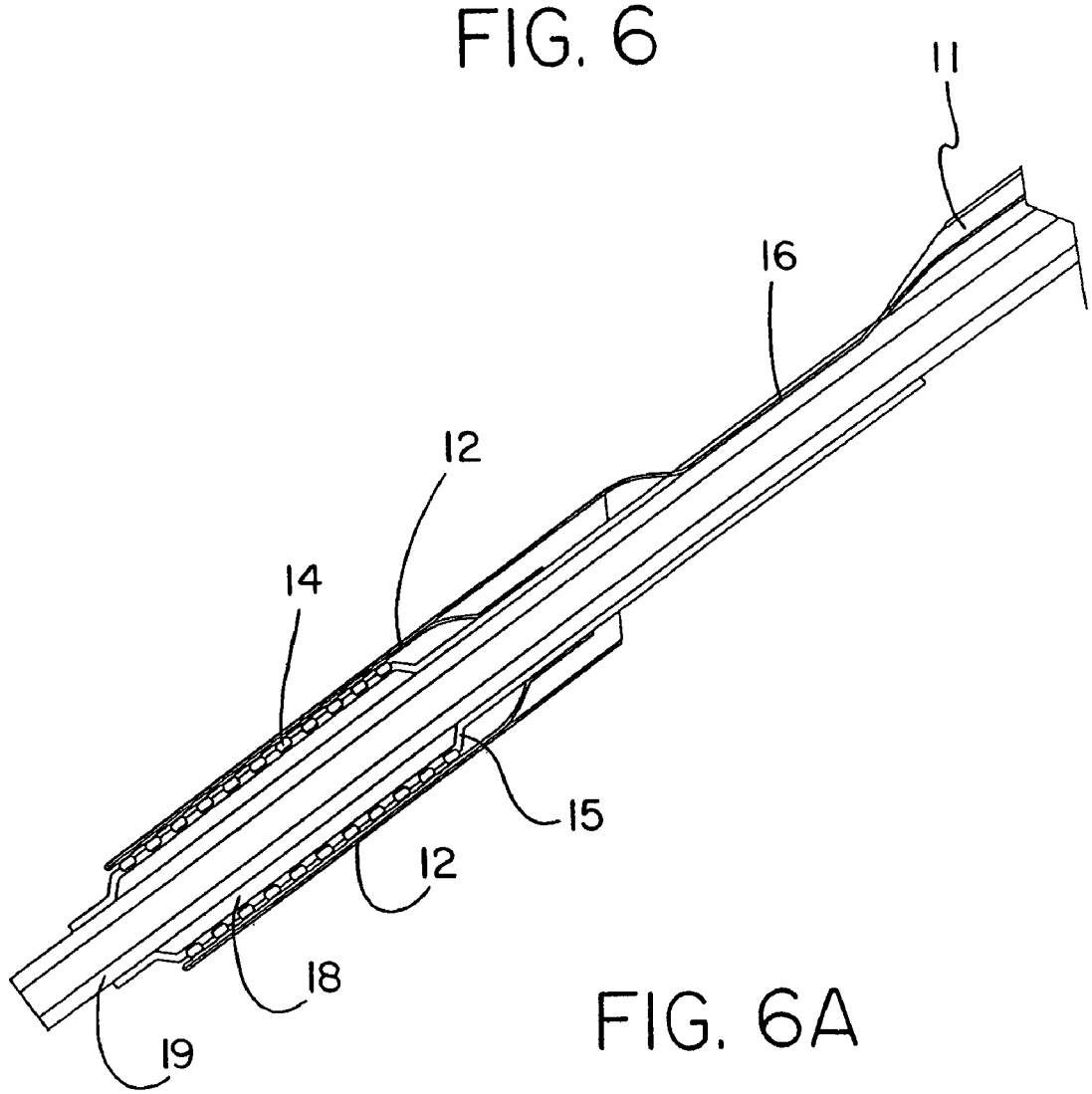
FIG. 6A is an enlarged view of FIG. 6.
Figure 7:
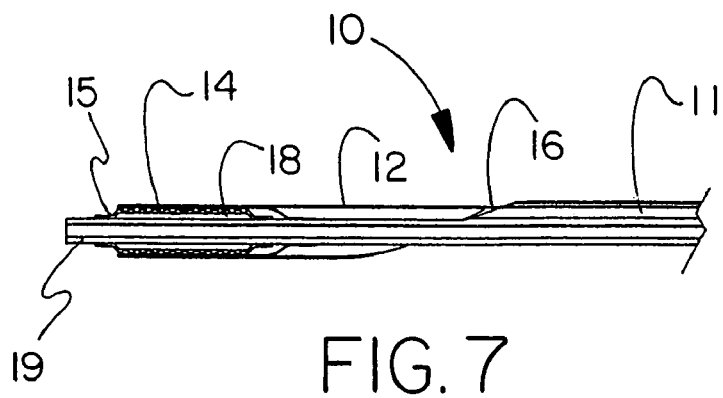
FIG. 7 illustrates a longitudinal cross-section of the present invention.
Figure 7A:
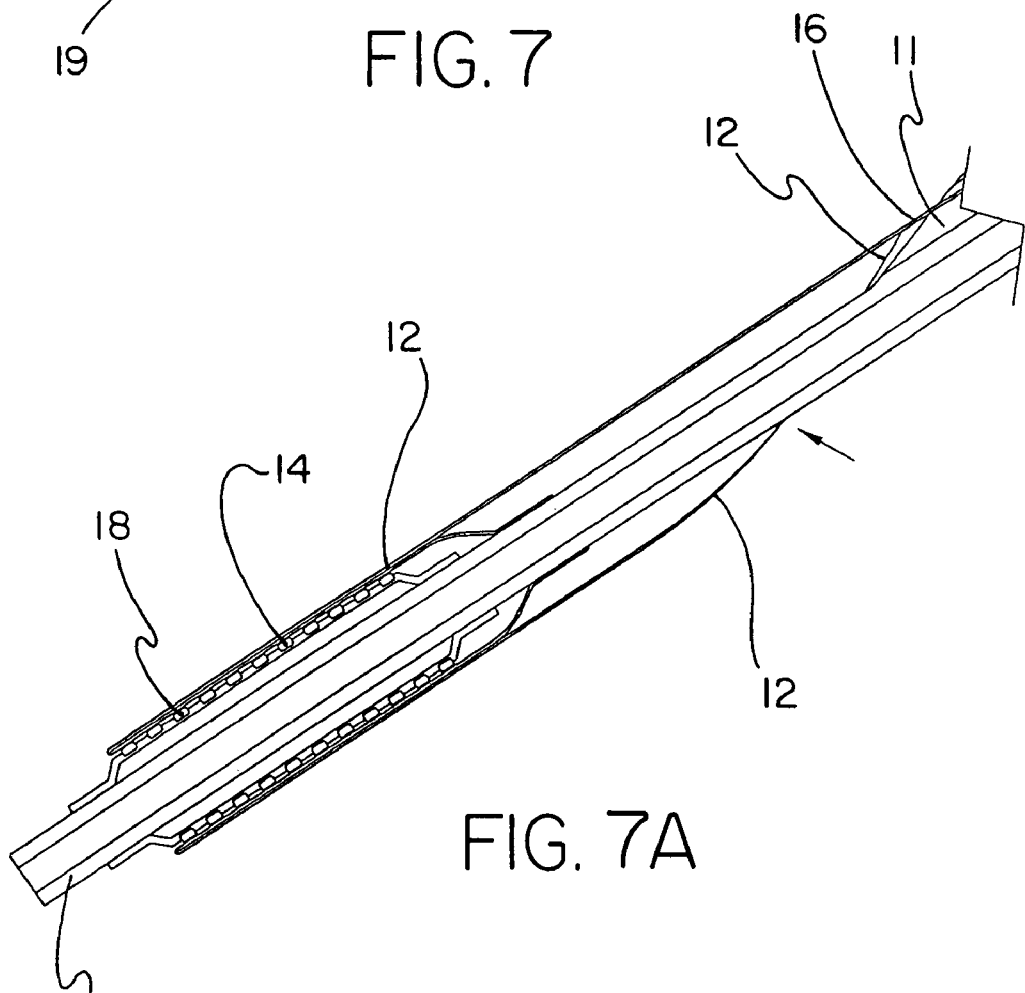
FIG. 7A is an enlarged view of FIG. 7.
Figure 7B:
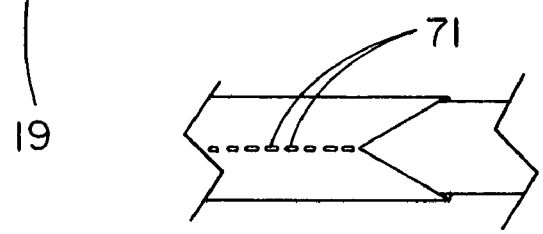
FIG. 7B illustrates the embodiment of FIG. 7A as viewed from the direction indicated by the arrow.
Figure 7C:
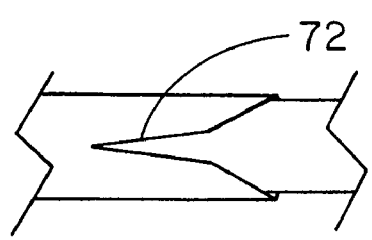
FIG. 7C illustrates the embodiment of FIG. 7A as viewed from the direction indicated by the arrow.
Figure 8:
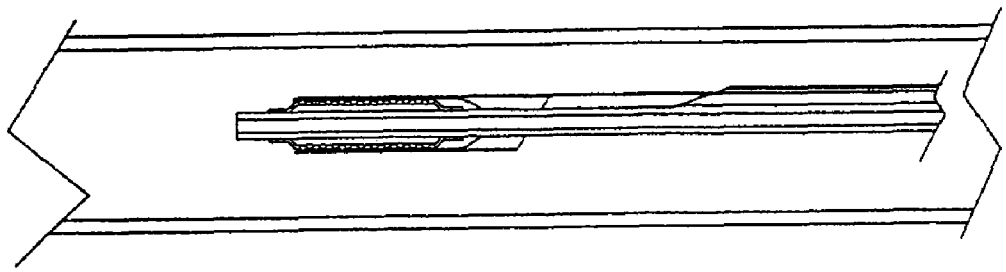
FIGS. 8 and 8A illustrate longitudinal cross-sections views of the present invention placed inside a vascular or cardiac structure.
Figure 8A:
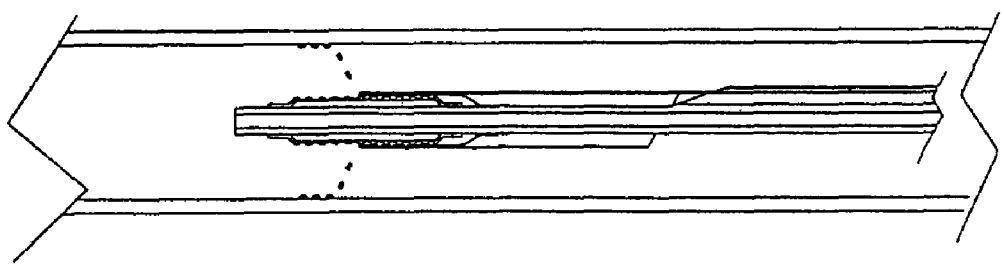

The sheath may be converted to deployment line by pulling on the deployment line and causing the sheath material to separate and converge into a single filament. As sheath material is converted to deployment line by this process, the edge of the sheath supplying material to the deployment line recedes causing the sheath to retract from around the expandable medical device. As a portion of the sheath retracts, the portion of the expandable medical device confined by the sheath is freed to expand (FIGS. 8-8A). Means are optionally provided to the deployment system that initiate or sustain the conversion of sheath to deployment line. As shown in FIG. 7, the means include perforations (71), cutouts (72), or other engineered defect introduced into the sheath material. As shown in FIG. 5, the means also include cutters (21) or other sharp edges on the delivery catheter. Such cutting means may be formed on the delivery catheter by exposing a strand of reinforcing stainless steel from within the catheter and adapting the strand to cut into the sheath portion.

Figure 9:
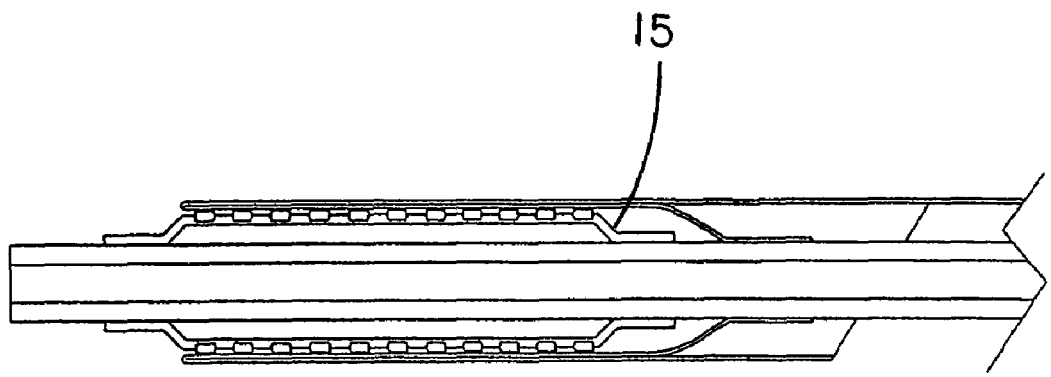
FIG. 9 illustrates a longitudinal cross-section of the present invention with a covering placed over an endoprosthesis mounting member.
Figure 9A:
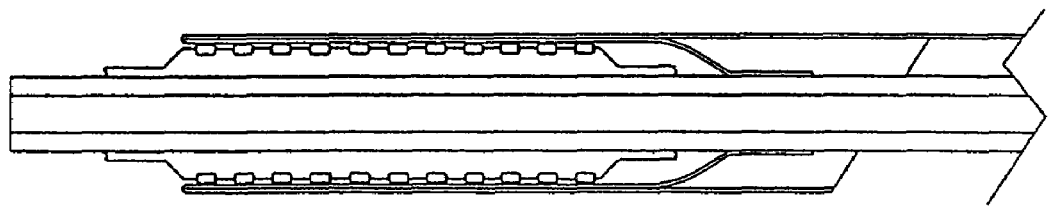
FIG. 9A illustrates a longitudinal cross-section of the present invention without a covering placed over an endoprosthesis mounting member.
Figure 10:
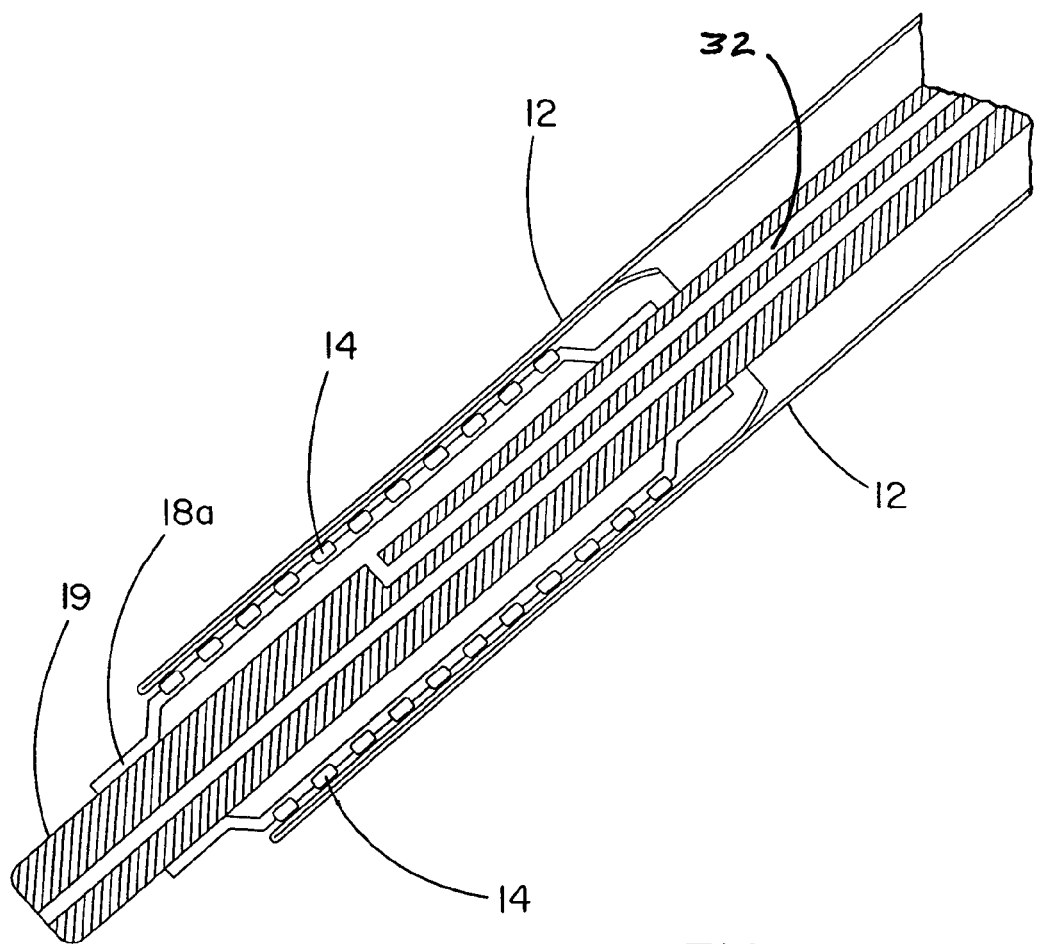
FIG. 10 illustrates a longitudinal cross-section of the present invention with an endoprosthesis mounting member placed between an underlying delivery catheter and an expandable medical device.

In the preferred embodiment of the present invention, materials, composites, constructions, and/or assemblies exhibiting compliance, compressibility, resilience, and/or expandability are placed between the expandable medical device and the delivery catheter to form an "endoprosthesis mounting member (18)." The endoprosthesis mounting member can be covered (15) or uncovered (FIG. 9). At least a portion of the expandable medical device is pressed into a covered or uncovered endoprosthesis mounting member to anchor the expandable medical device on the delivery catheter and prevent the expandable medical device from moving along the length of the catheter. Materials with a tacky surface are useful with the endoprosthesis mounting member, particularly in combination with a lubricious sheath material. The endoprosthesis mounting member eliminates the need for barrier, or retention, means placed at the proximal and distal end of the expandable medical device. In addition to added flexibility imparted to the deployment system without the barrier means, the profile of the sheath and expandable medical device combination is reduced without the barrier means. In yet another embodiment, the endoprosthesis mounting member is in the form of an inflatable balloon (FIG. 10, part 18a). Suitable materials for the endoprosthesis mounting member include, but are not limited to, silicones, silicone foams, polyurethane, polyurethane foams, and polytetrafluoroethylene foams or combinations thereof. The endoprosthesis mounting member is attached to the outer wall of the delivery catheter with adhesives, heat, or other suitable means. An inflatable endoprosthesis mounting member (18a) has at least one lumen in fluid communication with at least one lumen of the delivery catheter tube, which in turn, is in fluid communication with a pressurizable first chamber component (109) of a deployment assembly (100) of the present invention.

A non-inflatable endoprosthesis mounting member is preferably enclosed with a covering (15) in the form of a polymeric material. The polymeric material is preferably a fluoropolymer-based material. Porous expanded polytetrafluoroethylene is the preferred fluoropolymer for enclosing the compressible material. Other suitable polymeric materials include, but are not limited to, silicone, polyurethane, polyester, and the like.

Figure 10A:
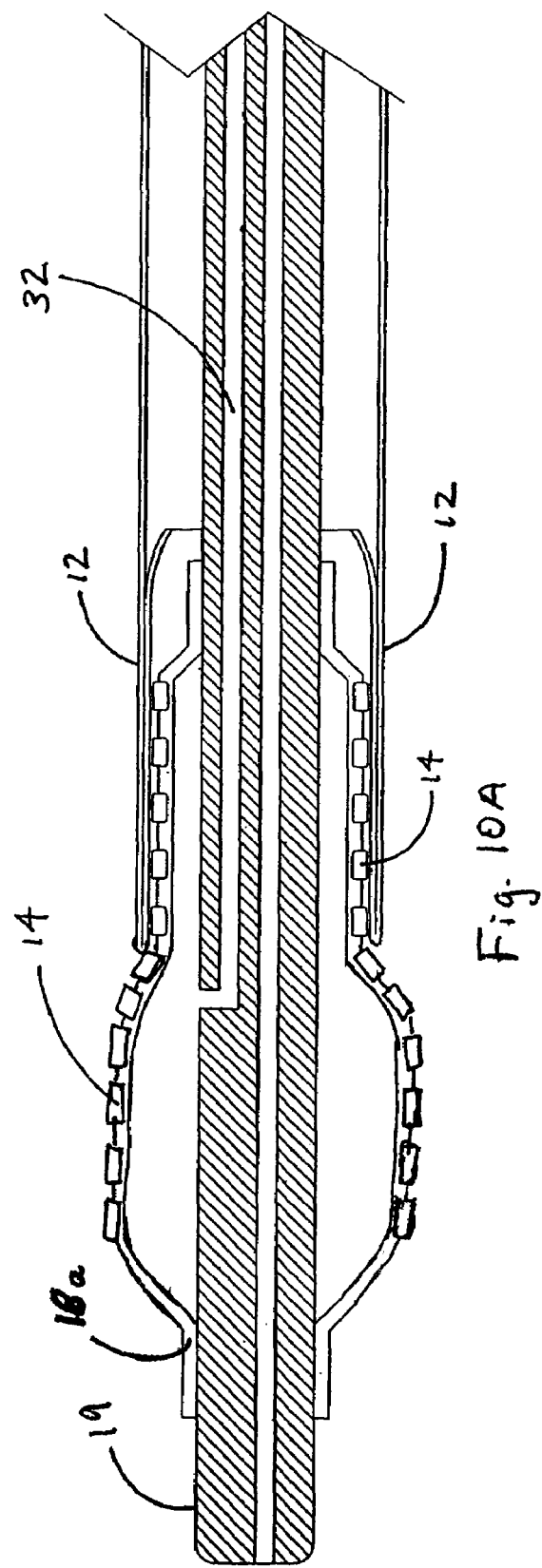
FIG. 10A illustrates the longitudinal cross-section of FIG. 10 with the endoprosthesis mounting member in a partially expanded configuration, the sheath in a partially retracted configuration, and the expandable medical device in a partially expanded configuration.
Figure 11:
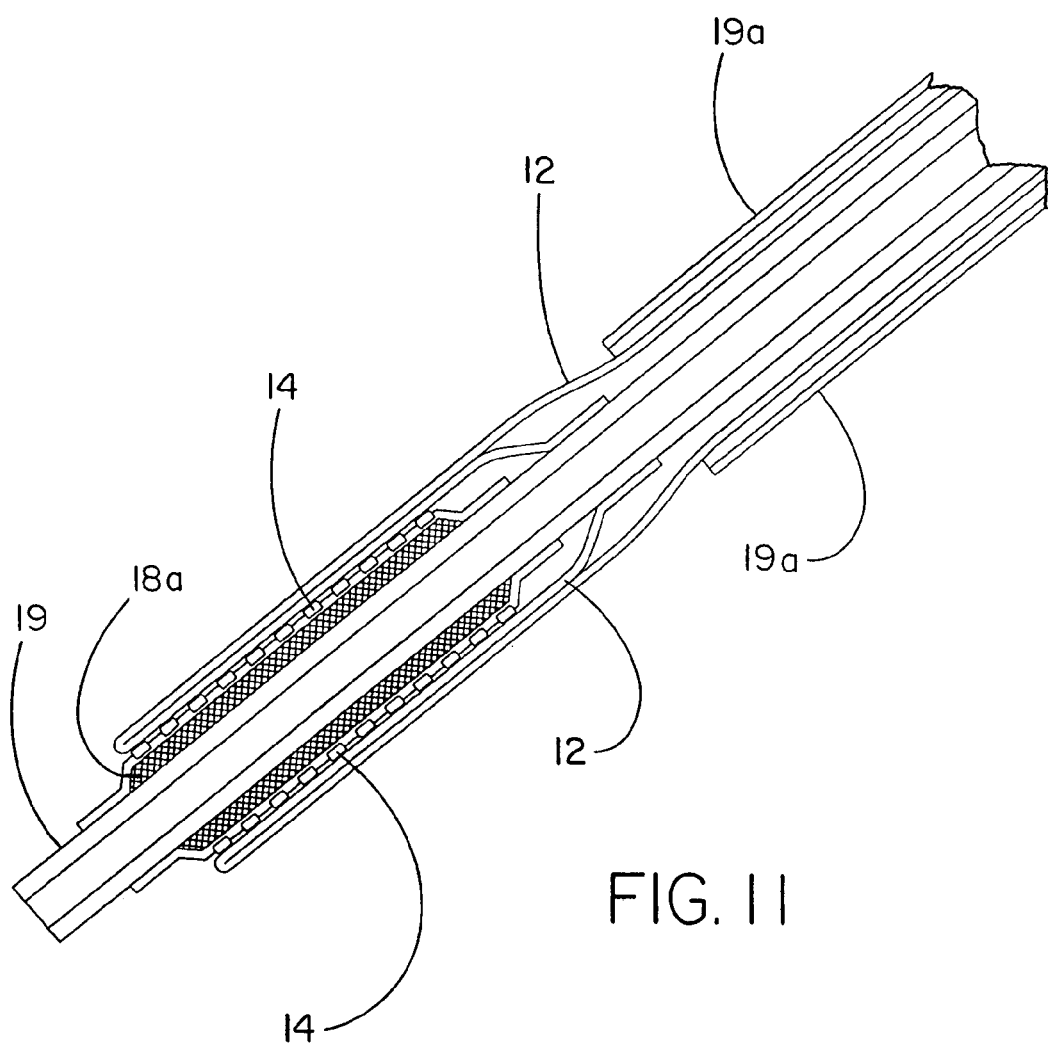
FIG. 11 illustrates a longitudinal cross-section of the present invention having an outer catheter, or tube, placed over substantially the entire length of a sheath-deployment line construction.

The present invention is also directed to a system for deploying the expandable medical device. Once the above-described expandable medical device deployment system is maneuvered to a desired location in a patient's vasculature, the system is activated to expand the endoprosthesis mounting member, while the sheath is simultaneously retracted from the expandable medical device. This step is often performed gradually to expose only portions of the expandable medical device at a time (FIG. 10A). The controlled deployment of the expandable medical device offered with the present invention permits the location of the device in the vasculature to be verified and adjusted, if necessary, before final deployment of the device. In some deployments, the sheath component of the system may become difficult to remove from an underlying expandable medical device. The deployment system of the present invention assists in such deployments by providing a mechanical advantage to the deployment line-sheath component that allows sufficient pulling force to be applied to the component to remove the sheath from the expandable medical device.

Preferred endoprosthesis mounting members are inflatable (18a). The inflatable endoprosthesis mounting member has a lumen (32) in fluid communication with a deployment assembly (100) of the present invention. Fluid in the form of gas or liquid is introduced into the endoprosthesis mounting member from a pressurizable first chamber (109, FIGS. 14-20) in the deployment assembly (100). As fluid pressure is generated in the first chamber (109), the pressure is transferred to the endoprosthesis mounting member (18a) where the pressure exerts force radially against an overlying expandable medical device (14). As the endoprosthesis mounting member becomes pressurized, an actuator (112, 116, 118, 120/122) coupled to the pressurization means (102/109) simultaneously begins to retract the sheath (12) from the expandable medical device (14). Further retraction of the sheath (12) allows the endoprosthesis mounting member to cause, assist, or permit radial expansion of exposed portions of the expandable medical device. Pressure is maintained in the endoprosthesis mounting member by the deployment assembly as the sheath is completely removed from the expandable medical device and the device fully deployed.

Retraction of the sheath is accomplished simultaneously with expansion of the endoprosthesis mounting member in the present invention by attaching the deployment line portion of the deployment line-sheath combination to an actuator that is mechanically coupled with a plunger, piston, or other fluid pressurization means. As seen in FIGS. 14-20, chamber (109) houses a plunger (102) attached to a first gear (104) or other screw means. The first gear (104) has a knob (106), handle, motor-drive coupler, or other activator for turning the first gear (104). A bevel, or similar, gear (108) engages the first gear (104) and is attached to an axle (110) that in turn in attached to an actuator (112, 116, 118, 120/122) for retracting a sheath from an expandable medical device. In one embodiment (FIG. 14), the actuator includes a rack and pinion gear arrangement attached to a deployment line (114). In another embodiment (FIG. 15), the actuator includes a deployment line (114) attached to a reel (116) connected to axle (110). In yet another embodiment (FIG. 16), the actuator includes deployment line (114) attached to a pulley (118).

In a preferred embodiment (FIG. 17), the actuator includes a deployment line (114) attached to a rod (120) connected to a piston (122) inside a second chamber (124) in fluid communication with the first chamber (109). As fluid pressure is increased in the first chamber (109), the pressure increases in both the endoprosthesis mounting member and the second chamber. Increased pressure in the second chamber causes the piston to move and pull on the deployment line. In turn, this causes the sheath to retract from the endoluminal device.

Figure 18:
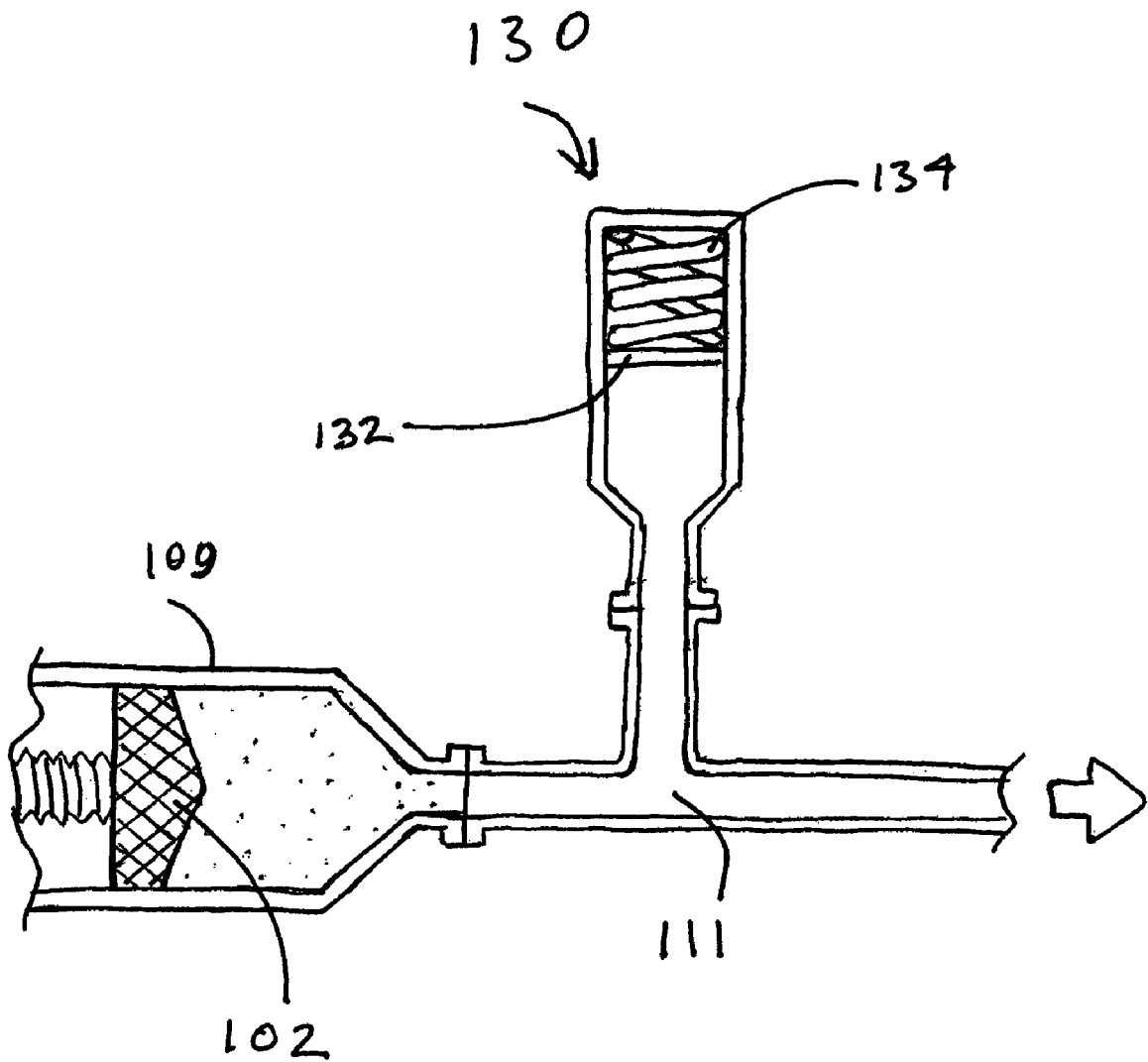
FIG. 18 illustrates a pressure storage component of the present invention.
Figure 19:
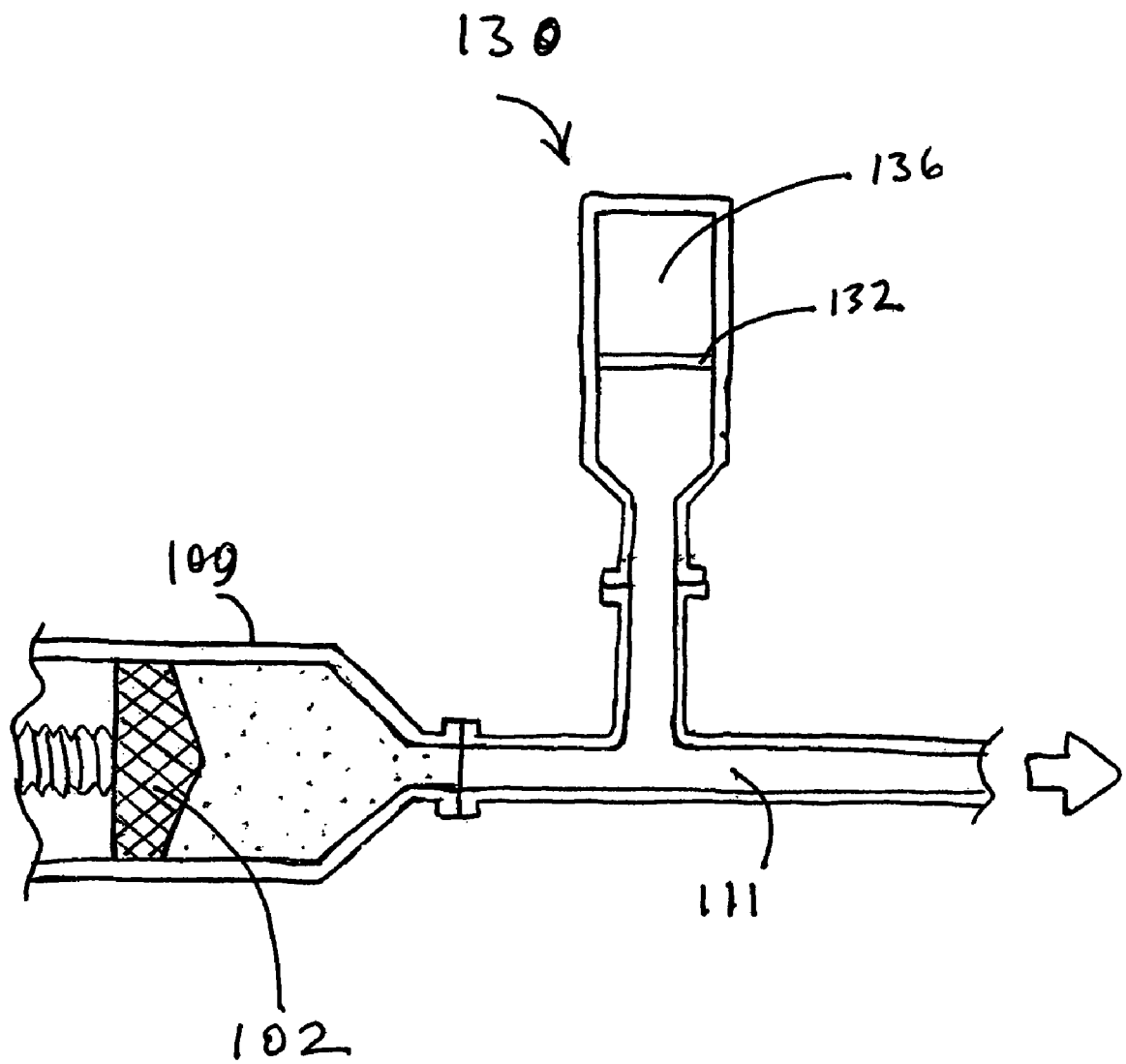
FIG. 19 illustrates a pressure storage component of the present invention.
Figure 20:
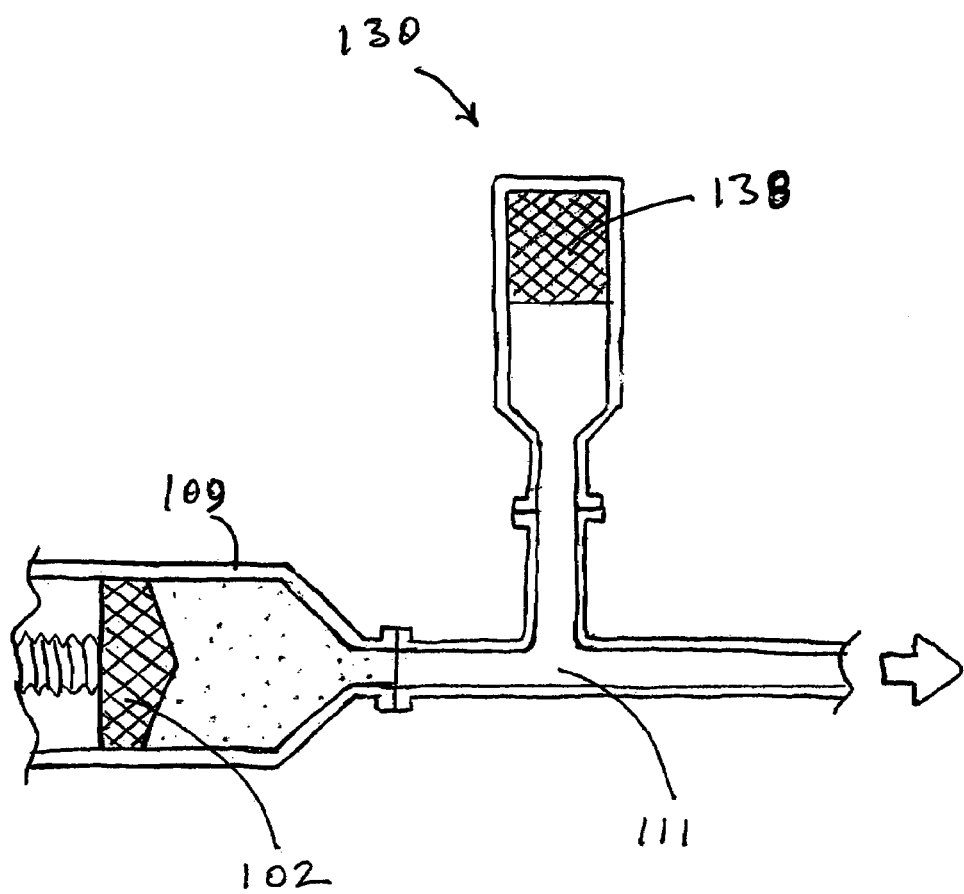
FIG. 20 illustrates a pressure storage component of the present invention.

In some situations, it may be desirable to pressurize and begin to expand an endoprosthesis mounting member before activating the deployment line and retracting the sheath. FIGS. 18-20 illustrate examples of pressure-storing apparatuses for use in pressurizing and expanding an endoprosthesis mounting member. FIG. 18 shows a third chamber (130) in fluid communication with the first chamber (109) having a diaphragm (132) having a spring (134) exerting mechanical force on the diaphragm (132). FIG. 19 shows a third chamber (130) in fluid communication with the first chamber (109) having a diaphragm (132) and a gas (136) exerting mechanical force on the diaphragm (132). FIG. 20 shows a third chamber (130) in fluid communication with first chamber (109) having a compressible material (138) in the third chamber (130).

Lastly, a contrast medium can be incorporated or introduced into the endoprosthesis mounting member to better visualize an overlying endoluminal device.

Although particular embodiments of the present invention have been shown and described, modifications may be made to the deployment system and assembly without departing from the spirit and scope of the present invention.

EXAMPLES

Example 1

This example describes the construction of a deployment system of the present invention. Construction of the system began with the preparation of a distal catheter shaft for receiving an expandable stent. Once the distal catheter was prepared, the expandable stent was placed within a sheath-deployment line. The distal catheter portion of this combination was attached to a primary catheter shaft. The deployment line portion was then routed through the primary catheter to a control knob. The control knob was part of a hub located proximally on the primary catheter. The sheath portion of the sheath-deployment line was in the form of a single-walled tube.

A tubular material three inches long was obtained from Burnham Polymeric, Inc., Glens Falls, N.Y. for use as the distal catheter shaft. The tube was made of a polyether block amide material, commonly known as PEBAX® resin and reinforced with a stainless steel braid. The outer diameter (OD) was 1.01 mm and the inner diameter (ID) was 0.76 mm. An endoprosthesis mounting member in the form of a compressible material was then placed on the catheter.

To place the endoprosthesis mounting member on the catheter, the catheter was mounted on a mandrel having an outer diameter of 0.74 mm. A film of porous expanded polytetrafluoroethylene (ePTFE) was obtained according to the teachings in U.S. Pat. No. 5,814,405, issued to Branca, which is incorporated herein by reference. A discontinuous coating of fluorinated ethylene propylene (FEP) was applied to one side of the ePTFE material in accordance with U.S. Pat. No. 6,159,565, issued to Campbell et al., and incorporated herein by reference. An edge of the ePTFE-FEP composite film two inches wide was attached with heat to the catheter shaft. After initial attachment, the film was wrapped around the catheter shaft forty-five (45) times under light tension. With every fifth wrap of the film, and on the final layer, the film is further attached to itself with heat supplied by a soldering iron.

This procedure provided a endoprosthesis mounting member in the form of a compressible material, or compliant "pillow," on the distal catheter shaft. The expandable stent was mounted over the endoprosthesis mounting member. The endoprosthesis mounting member provides a means of retaining an expandable stent on the catheter shaft during storage, delivery to an implantation site, and deployment of the expandable stent at the implantation site. Optionally, the endoprosthesis mounting member may be reinforced with a thin coating of an elastomeric material such as silicone, urethane, and/or a fluoroelastomer.

An eight (8) cell, 6 mm diameter, nitinol stent was obtained from Medinol Ltd., Tel-Aviv, Israel. The stent was placed over the endoprosthesis mounting member of the catheter in an expanded state. The combination was placed within a machine having a mechanical iris that compacts or compresses the stent portion of the assembly onto the endoprosthesis mounting member. While retained in the mechanical iris machine, the stent was reduced in temperature from room temperature (c. 22° C.) to approximately five degrees centigrade (5° C.). At the reduced temperature, the iris machine was actuated to compact, or collapse, the stent onto the endoprosthesis mounting member. While in the refrigerated and compressed configuration, the catheter, endoprosthesis mounting member, and stent were placed within a sheath-deployment line of the present invention.

The sheath-deployment line having a length equal to, or greater than, the length of the final deployment system was made as follows. A length of stainless steel mandrel (c. 1 m) measuring 1.89 mm in diameter was covered with a tubular extruded ePTFE material having an overall length of about 200 cm. The tubular ePTFE material had an outer diameter of 1.41 mm, a wall thickness of 0.05 mm, and an average longitudinal tensile strength of 3.52 kgf with an average circumferential strength of 0.169 kgf. The tubular ePTFE material also had an average mass/length of 0.0473 g/ft with an average Matrix Tensile Strength of 69,125 PSI. At one end (proximal end), the tubular ePTFE material was bunched together on the mandrel, while the opposite end (distal end) of the ePTFE material remained smooth on the mandrel.

The first few centimeters of the tubular ePTFE material was sacrificed and the next 5 cm of the distal end (smoothed end) of the extruded ePTFE material was then reinforced with a composite fluoropolymer material as follows. The ePTFE-covered mandrel was attached to retaining chucks on a film-wrapping machine. A first reference line located approximately 5 cm from the end of the smooth portion of the extruded ePTFE material was circumferentially drawn around the material with a permanent marker (SHARPIE®). A 5 cm wide composite membrane made of expanded polytetrafluoroethylene (ePTFE) and fluorinated ethylene propylene (FEP) was applied proximal from the first reference line on the extruded ePTFE material so the FEP portion of the composite membrane was against the extruded ePTFE material. The composite membrane was wrapped around the ePTFE covered mandrel two times so that the primary strength of the extruded ePTFE material was oriented perpendicular to the longitudinal axis of the mandrel. The composite membrane was initially tacked in place on the extruded ePTFE material with heat applied from a soldering iron. The composite ePTFE/FEP material had a density of about 2.14 g/cm³, a thickness of 0.005 mm, and tensile strengths of about 340 KPa (about 49,000 psi) in a first direction and of about 120 KPa (about 17,000 psi) in a second direction (perpendicular to the first direction). The tensile measurements were performed on an Instron Tensile Machine (Instron Corporation, Canton, Mass.) at 200 mm/min. load rate with 2.5 cm (one inch) jaw spacing.

Material of the sheath-deployment line construction adjacent to the reinforced portion was smoothed out along the mandrel and a second reference line was drawn around the material 5 cm from the first reference line.

A second portion of the sheath-deployment line construction was reinforced as follows. A second reference line was drawn around the extruded ePTFE material 5 cm from the proximal end of the first reinforced portion. Using the second reference line to align a 2 cm wide strip of the above-mentioned ePTFE/FEP composite membrane, the composite membrane was wrapped once around the remaining portion of the extruded ePTFE material to form a second reinforced portion of the sheath-deployment line of the present invention. The second reinforced portion was about 2 cm in length. The composite reinforcing membrane material was attached to the extruded ePTFE material as described above, with the exception that the major strength component of the material was parallel to the axis of the mandrel.

Any air trapped in the construction was removed by applying a sacrificial layer of ePTFE tightly around the construction. A one inch (2.54 cm) wide film of ePTFE was helically overwrapped around the reinforced portion of the construction. Two layers of the ePTFE film were applied in one direction and two layers were applied in the opposite direction. The construction with sacrificial layers were then placed in an oven heated to 320° C. for eight minutes. Upon removal from the heated oven, the combination was allowed to cool to room temperature. The sacrificial ePTFE material was then removed.

The construction was then removed from the mandrel and another mandrel (1.83 mm diameter×30.5 cm long) inserted into the reinforced end of the construction. With the mandrel supporting the reinforced end, a 5 mm long slit was made proximal to the reinforced portion of the sheath-deployment line construction. A second mandrel was placed inside the construction up to the 5 mm slit where it exited the construction. The proximal portion of the sheath-deployment line construction was converted into a filament by placing the proximal end into the chucks of the film wrapper chucks and rotating the film wrapper approximately 2,800 times while the mandrel with the reinforced construction was immobilized. After the construction was spun into a filament, the filament was strengthened by briefly applying heat to the filament with a soldering iron set at 450° C. The strengthened filament was smoothed and rendered more uniform in diameter by passing the filament over a 1.8 cm diameter×3.8 cm long dowel heated to approximately 320° C. The filament was passed over the heated dowel at a 45° angle under slight tension. This process was repeated two more times over the entire length of the filament.

The filament portion of the sheath-deployment line of the present invention was routed through a lumen of a primary catheter and connected to a control knob. The control knob was part of a hub located at the proximal end of the primary catheter. When the deployment line portion of the sheath-deployment line was pulled, the sheath portion was retracted from around the stent.

Example 2

This example describes the construction of a deployment system of the present invention. Construction of the system begins with the preparation of a distal catheter shaft for receiving an expandable stent. Once the distal catheter was prepared, the expandable stent was placed within a sheath-deployment line. The distal catheter portion of this combination was attached to a primary catheter shaft. The deployment line portion was then routed through the primary catheter to a control knob. The control knob was part of a hub located proximally on the primary catheter. The sheath portion of the sheath-deployment line was in the form of a double-walled tube.

A tubular material three inches long was obtained from Burnham Polymeric, Inc., Glens Falls, N.Y. for use as the distal catheter shaft. The tube was made of a polyether block amide material, commonly known as PEBAX® resin and reinforced with a stainless steel braid. The outer diameter (OD) was 1.01 mm and the inner diameter (ID) was 0.76 mm. A endoprosthesis mounting member in the form of a compressible material was then placed on the catheter. To place the endoprosthesis mounting member on the catheter, the catheter was mounted on a mandrel having an outer diameter of 0.74 mm. A film of porous expanded polytetrafluoroethylene (ePTFE) was obtained according to the teachings in U.S. Pat. No. 5,814,405, issued to Branca, which is incorporated herein by reference. A discontinuous coating of fluorinated ethylene propylene (FEP) was applied to one side of the ePTFE material in accordance with U.S. Pat. No. 6,159,565, issued to Campbell et al., which is incorporated herein by reference. An edge of the ePTFE-FEP composite film two inches wide was attached with heat to the catheter shaft. After initial attachment, the film was wrapped around the catheter shaft forty-five (45) times under light tension. With every fifth wrap of the film, and on the final layer, the film is further attached to itself with heat. This procedure provides a endoprosthesis mounting member on the distal catheter shaft. The expandable stent is mounted over the endoprosthesis mounting member. The endoprosthesis mounting member provides a means of retaining an expandable stent on the catheter shaft during storage, delivery to an implantation site, and deployment of the expandable stent at the implantation site. Optionally, the endoprosthesis mounting member may be reinforced with a thin coating of an elastomeric material such as silicone, urethane, and/or a fluoroelastomer.

An eight (8) cell, 6 mm diameter, nitinol stent was obtained from Medinol Ltd., Tel-Aviv, Israel. The stent was placed over the endoprosthesis mounting member of the catheter in an expanded state. The combination was placed within a machine having a mechanical iris that compacts or compresses the stent portion of the assembly onto the endoprosthesis mounting member. While retained in the mechanical iris machine, the stent was reduced in temperature from room temperature to approximately five degrees centigrade (5° C.). At the reduced temperature, the iris machine was actuated to compact, or collapse, the stent onto the endoprosthesis mounting member. While in the refrigerated, compressed configuration, the catheter, endoprosthesis mounting member, and stent were placed within a sheath-deployment line of the present invention.

The sheath-deployment line having a length equal to, or greater than, the length of the final deployment system was made as follows. A stainless steel mandrel measuring 1.73 mm in diameter was covered with a sacrificial layer of ePTFE. The sacrificial ePTFE material aids in removal of the sheath-deployment line from the mandrel. Two wraps of a thin, polytetrafluoroethylene (PTFE) membrane were applied to the mandrel. The ePTFE membrane was applied so the primary strength of the film was oriented parallel with the longitudinal axis of the mandrel. The film was initially tacked in place with heat applied with a soldering iron. The membrane thickness measured about 0.0002" (0.005 mm) and had tensile strengths of about 49,000 psi (about 340 KPa) in a first direction and of about 17,000 psi (about 120 KPa) in a second direction (perpendicular to the first direction). The tensile measurements were performed at 200 mm/min. load rate with a 1" (2.5 cm) jaw spacing. The membrane had a density of about 2.14 g/cm$^3$. The membrane was further modified by the application of an FEP coating on one side in accordance with U.S. Pat. No. 6,159,565, issued to Campbell et al., which is incorporated herein by reference. Next, two wraps of another ePTFE film made according to the teachings of Bacino in U.S. Pat. No. 5,476,589 and further modified with a discontinuous layer of an FEP material applied to one side of the ePTFE film were applied to one end of the construction (approx. 1" wide). U.S. Pat. No. 5,476,589 is incorporated herein by reference. These two wraps had the primary strength direction of the film oriented perpendicular to the mandrel's longitudinal axis. These layers of film provide additional "hoop" or "radial" strength to the sheath-deployment line construct. The mandrel and sheath-deployment line construct were placed in an air convection oven obtained from The Grieve Corporation, Round Lake, Ill., and subjected to a thermal treatment of 320° C. for 12 minutes. After air cooling, the ePTFE/FEP tube construct was removed from the mandrel and the sacrificial ePTFE layer removed. In this example, a length of sheath-deployment line extending beyond the end of the stent was provided. The additional length of sheath-deployment line was folded back over sheath portion enclosing the stent to form a double-walled construct. The double-walled sheath-deployment line had an inner wall and an outer wall. The inner wall was against the stent and the outer wall included the integral deployment line portion of the construct. The construct was then attached to a primary catheter shaft using heat and standard materials.

The deployment line portion of the sheath-deployment line was made by splitting the sheath-deployment line along its length from a proximal end up to, but not including, the sheath portion enclosing the stent. The material thus obtained was gathered into a filament by rolling the material. Heat was applied to the material to set the material in the filamentous form. The deployment line filament was routed through a lumen in the primary catheter and connected to a control knob. The control knob was part of a hub located at the proximal end of the primary catheter. When the deployment line portion of the sheath-deployment line was pulled, the sheath portion was retracted from around the stent.

Example 3

This example describes the incorporation of a means for initiating or maintaining conversion of the sheath portion of the sheath-deployment line to deployment line by introducing perforations and intentional stress risers into the sheath.

The sheath-deployment line from Example 2 is modified as follows. Prior to rolling the sheath portion into a double-walled construct and loading the stent therein, the sheath is perforated and/or supplied with "stress risers" that facilitate in separation of the tubular sheath upon retraction of the deployment line portion. An appropriate laser for making the perforations or stress risers is a 20 watt $CO_2$ laser obtained from Universal Laser Systems, Scottsdale, Ariz. To form the perforations in the sheath portion, the sheath is placed on a sandblasted stainless steel mandrel and exposed to the laser to cut a series of holes in a part of the tube that will subsequently serve as the outer wall of the double-walled construct. The geometry of the holes can be varied depending on the application. The perforated sheath portion is used on a deployment line system of the present invention as described in Example 2. In this example, tension applied to the deployment line portion at the hub end of the catheter results in retraction of the sheath from around the stent and also results in parting the sheath at the perforations. As the sheath portion is separated, the sheath material becomes convertible to deployment line.

Example 4

This example describes the incorporation of a means for initiating or maintaining conversion of the sheath portion of the sheath-deployment line to deployment line by the use of an appropriate splitting means.

The primary catheter from Example 2 is modified as follows. The primary portion of the catheter is provided with a notch in the wall in 180 degrees opposition and slightly distal to the entry point of the deployment line portion into the catheter lumen. The notch is further modified to provide a small cutting edge in the notch. In one embodiment, the cutting edge is simply attached to the notch with heat, adhesives, and the like. In another embodiment, the cutting edge is formed by exposing a portion of a metallic braid used to reinforce the catheter shaft and forming the braid into a cutting edge. In this example, tension applied to the deployment line portion at the hub end of the catheter results in retraction of the sheath from around the stent and also results in parting the sheath at the perforations. As the sheath portion is separated, the sheath material becomes convertible to deployment line.

Example 5

This example describes the construction of a deployment system of the present invention for use in the delivery and deployment of both self-expanding as well as balloon expandable devices. The deployment system of this example utilizes an endoprosthesis mounting member in the form of an inflatable balloon.

A sheath-deployment line having a length equal to, or greater than, the length of the final deployment system is made as follows. A stainless steel mandrel measuring 1.73 mm in diameter is covered with a sacrificial tube of ePTFE. The sacrificial ePTFE material aids in removal of the sheath-deployment line from the mandrel. Two wraps of a thin, polytetrafluoroethylene (PTFE) membrane is applied to the mandrel. The ePTFE membrane is applied so the primary strength of the film is oriented parallel with the longitudinal axis of the mandrel. The film is initially tacked in place with heat applied with a soldering iron. The membrane thickness measured about 0.0002" (0.005 mm) and had tensile strengths of about 49,000 psi (about 340 KPa) in a first direction and about 17,000 psi (about 120 KPa) in a second direction (perpendicular to the first direction). The tensile measurements are performed at 200 mm/min. load rate with a 1 inch (2.5 cm) jaw spacing. The membrane has a density of about 2.14 g/cm$^3$. The membrane is further modified by the application of a fluorinated ethylene propylene (FEP) coating on one side in accordance with U.S. Pat. No. 6,159,565, issued to Campbell et al. and incorporated herein by reference. Next, two wraps of another ePTFE film made according to the teachings of Bacino in U.S. Pat. No. 5,476,589, which is incorporated herein by reference, and further modified with a discontinuous layer of an FEP material applied to one side of the ePTFE film are applied to one end of the construction (approx. 1" wide). These two wraps have the primary strength direction of the film oriented perpendicular to the mandrel's longitudinal axis. These layers of film provide additional "hoop" or "radial" strength to the sheath-deployment line construct. The mandrel and sheath-deployment line construct are placed in an air convection oven obtained from The Grieve Corporation, Round Lake, Ill., and subjected to a thermal treatment of 320° C. for 12 minutes. After air cooling, the ePTFE/FEP tube construct is removed from the mandrel and the sacrificial ePTFE layer removed. Placement of this construct over an expandable stent and formation of a deployment line portion therefrom is described below.

As seen in FIG. 10, a balloon expandable NIRflex™ stent (14), available from Medinol Ltd, Tel-Aviv, Israel, is placed over and compacted around a deflated and collapsed angioplasty balloon mounted on a delivery catheter shaft (19). The angioplasty balloon is made in accordance with U.S. Pat. No. 5,752,934 to Campbell et al., which is incorporated herein by reference, and available from W.L. Gore & Associates, Inc., Flagstaff, Ariz. under the tradename APTERA® angioplasty balloon. The APTERA® angioplasty balloon serves as an endoprosthesis mounting member (18a) for receiving and retaining the compacted stent (14).

While the stent is confined in a compacted configuration, a length of sheath-deployment line (12) is placed over the compacted stent and extended beyond the end of the stent. The additional length of sheath-deployment line is folded back over sheath portion enclosing the stent to form a double-walled construction. The double-walled sheath-deployment line has an inner wall and an outer wall. The inner wall is against the stent and the outer wall includes the integral deployment line portion of the construct.

The deployment line portion of the sheath-deployment line is made by splitting the sheath-deployment line along its length from the proximal end toward the distal end for a distance. The slit can range in length from about one centimeter to substantially the entire length of the sheath-deployment line construction up to, but not including, the sheath portion enclosing the stent. It is preferred to form the deployment line portion near the proximal end of the delivery catheter. The material thus obtained is gathered into a filament by rolling the material. Heat is applied to the material to set the material in the filamentous form. The sheath-deployment line is routed through a dedicated lumen in the delivery catheter and exits at a hub where the deployment line portion is attached to a control knob. The control knob is part of a hub located at the proximal end of the primary catheter. When tension is applied to the deployment line portion of the sheath-deployment line, the sheath portion retracts from around the stent. Removal of the sheath portion from the underlying stent frees the stent to expand. The NIRflex™ stent of this example is expanded by inflating the APTERA® angioplasty balloon. Once the stent is expanded, the balloon is deflated and the delivery catheter along with the sheath-deployment line construction removed from the implant recipient. When self-expanding stents are used in the present invention, the balloon is useful as an endoprosthesis mounting member.

Example 6

This example describes the construction of a deployment system of the present invention utilizing a deployment assembly of the present invention.

A deployment system according to any of the above-examples can be used with a deployment assembly of the present invention. For purposes of illustration, this example will be described with reference to the deployment system described in Example 5 having an endoprosthesis mounting member in the form of an inflatable balloon.

As seen in FIGS. 14-17, a deployment assembly of the present invention (100) is configured to be connected to a delivery catheter (101) so a lumen (111) of the delivery catheter is in fluid communication (32) with the inflatable endoprosthesis mounting member described in Example 5 and a first pressurizable chamber (109) of the deployment assembly (100).

In this example, the first pressurizable chamber (109) in the form of a plastic syringe was fitted with a rubber plunger (102) attached to a means for moving the plunger in the chamber (104, 106) to generate, maintain, or reduce pressure in the deployment system. Means for actuating the deployment line portion were provided in the form of second pressurizable chamber (124) in fluid communication with the first pressurizable chamber (109). The second pressurizable chamber in the form of a plastic syringe was provided with a moveable rubber piston (122) placed therein and attached to the deployment line portion through a plastic connecting rod (120).

As plunger (102) was moved into the first pressurizable chamber (109), fluid pressure increased in the chamber (102), the catheter lumen (111), and the endoprosthesis mounting member causing the endoprosthesis mounting member to exert radial force against the overlying balloon expandable NIRflex™ stent (14). Simultaneously, fluid pressure in the second pressurizable chamber (124) increased and began to move piston (122) actuating the attached deployment line (114) and retracting the sheath from the balloon expandable NIRflex™ stent (14).

Example 7

In this example, a deployment system of the present invention is further fitted with a pressure-storing apparatus. As shown in FIGS. 18-20, various pressure-storing apparatuses can be affixed to the deployment system in fluid communication with an endoprosthesis mounting member.

The pressure-storing apparatus (130) of this example is made by attaching a plastic syringe to the deployment system having a diaphragm (132) in the form of a movable rubber plunger in the syringe. The diaphragm (132) defines a first airtight chamber (139) containing compressible gas (136) and a second chamber (137) in fluid communication with a lumen of an inflatable endoprosthesis mounting member (18a). The compressible gas (136) in the first chamber (139) is increased in pressure as pressure is increased in the pressurizable chamber (109) and the endoprosthesis mounting member (18a). Once application of pressure in the pressurizable chamber (109) is stopped, the compressed gas (136) in the first airtight chamber (139) presses against the diaphragm (132) and exerts pressure on fluid in the deployment system to maintain or increase fluid pressure in the endoprosthesis mounting member (18a).

While particular embodiments of the present invention have been illustrated and described herein, the present invention should not be limited to such illustrations and descriptions. It should be apparent that changes and modifications may be incorporated and embodied as part of the present invention within the scope of the following claims.

The invention claimed is:

1. A deployment system for an endoluminal device comprising:
    an expandable endoluminal device mounted on a distal end of a delivery catheter provided with an endo-prosthesis mounting member;
    a removable sheath in the form of a continuous double-walled tube adapted to cover and constrain at least a portion of said endoluminal device in an introductory profile;
    wherein said deployment system includes a deployment line integral with and extending from one wall of said double-walled tube to which tension can be applied to aid endoluminal device deployment;
    wherein upon endoluminal device deployment, said double-walled tube progressively unrolls from around said endoluminal device through actuation of said deployment line to form removed sheath material;
    wherein said removed sheath material begins to become converted to deployment line at a point where said removed sheath material breaks apart, separates, and converges into deployment line material in the form of an elongated filament;
    wherein said converged deployment line material is removed from said deployment system along with said deployment line;
    wherein said deployment line is attached to an actuator at a proximal end of said catheter tube, wherein said actuator is coupled to a means in fluid communication with a lumen of said endoprosthesis mounting member for expanding said endoprosthesis mounting member, whereby said endoprosthesis mounting member is expanded simultaneously with unrolling of said overlying sheath from said expandable medical device.

2. The implantation system of claim 1 further comprising a pressurizable chamber attached to said system in fluid communication with said endoprosthesis mounting member.

3. The implantation system of claim 2 wherein said pressurizable chamber comprises a diaphragm having a compressible material in contact with said diaphragm.

4. The implantation system of claim 3 wherein said compressible material is a spring.

5. The implantation system of claim 3 wherein said compressible material is a gas.

6. The implantation system of claim 3 wherein said compressible material is a polymeric material.

7. The deployment assembly of claim 1 further comprising a pressure-storage chamber in fluid communication with said means for expanding said endoprosthesis mounting member.

8. The medical device deployment system of claim 1 further comprising a gas bladder placed within said means for expanding said endoprosthesis mounting member.

* * * * *